United States Patent [19]

Lok et al.

[11] Patent Number: 4,684,617

[45] Date of Patent: Aug. 4, 1987

[54] TITANIUM-ALUMINUM-PHOSPHORUS-SILICON-OXIDE MOLECULAR SIEVES

[75] Inventors: Brent M. T. Lok, New City; Bonita K. Marcus, Rye; Edith M. Flanigen, White Plains, all of N.Y.

[73] Assignee: Union Carbide Corporation, Danbury, Conn.

[21] Appl. No.: 600,179

[22] Filed: Apr. 13, 1984

[51] Int. Cl.⁴ .................... B01J 27/14; C01B 25/36
[52] U.S. Cl. .................................. 502/214; 423/306
[58] Field of Search ............. 423/305, 306, 326, 328, 423/329; 502/60, 62, 77, 162, 164, 208, 214

[56] References Cited

U.S. PATENT DOCUMENTS

| | | | |
|---|---|---|---|
| 4,310,440 | 1/1982 | Wilson et al. | 423/305 X |
| 4,440,871 | 4/1984 | Lok et al. | 502/214 |
| 4,500,651 | 2/1985 | Lok et al. | 502/208 |

FOREIGN PATENT DOCUMENTS

| | | | |
|---|---|---|---|
| 0054364 | 6/1982 | European Pat. Off. | |
| 0055046 | 6/1982 | European Pat. Off. | |
| 0055529 | 7/1982 | European Pat. Off. | |
| 0059059 | 9/1982 | European Pat. Off. | |
| 0132550 | 2/1985 | European Pat. Off. | 423/328 M |
| 3128988 | 2/1983 | Fed. Rep. of Germany | 423/328 M |
| 3141283 | 4/1983 | Fed. Rep. of Germany | 423/328 |
| 1531775 | 7/1968 | France | 423/328 M |
| 2024790 | 1/1980 | United Kingdom | 423/326 |

OTHER PUBLICATIONS

Haggin, C & EN, Jun. 30, 1983, pp. 36 & 37.

Primary Examiner—William R. Dixon, Jr.
Assistant Examiner—R. Bruce Breneman
Attorney, Agent, or Firm—Vincent J. Vasta, Jr.

[57] ABSTRACT

Crystalline molecular sieves having three-dimensional microporous framework structures of $TiO_2$, $AlO_2$, $SiO_2$ and $PO_2$ tetrahedral units are disclosed. These molecular sieves have an empirical chemical composition on an anhydrous basis expressed by the formula:

$$mR:(Ti_wAl_xP_ySi_z)O_2$$

wherein "R" represents at least one organic templating agent present in the intracrystalline pore system; "m" represents the molar amount of "R" present per mole of $(Ti_wAl_xP_ySi_z)O_2$; and "w", "x", "y" and "z" represent the mole fractions of titanium, aluminum, phosphorus and silicon, respectively, present as tetrahedral oxides. Their use as adsorbents, catalysts, etc. is also disclosed.

38 Claims, 3 Drawing Figures

TITANIUM-ALUMINUM-PHOSPHORUS-SILICON-OXIDE MOLECULAR SIEVES

FIELD OF THE INVENTION

The instant invention relates to a novel class of crystalline microporous molecular sieves, and to the method of their preparation. The invention relates to novel titanium-aluminum-phosphorus-silicon-oxide molecular sieves having titanium, aluminum, phosphorus and silicon in the form of framework tetrahedral oxides. These compositions may be prepared hydrothermally from gels containing reactive compounds of titanium, aluminum, phosphorus and silicon capable of forming a framework tetrahedral oxides, and preferably at least one organic templating agent which functions in part to determine the course of the crystallization mechanism and the structure of the crystalline product.

BACKGROUND OF THE INVENTION

Molecular sieves of the crystalline aluminosilicate zeolite type are well known in the art and now comprise over 150 species of both naturally occurring and synthetic compositions. In general the crystalline zeolites are formed from corner-sharing $AlO_2$ and $SiO_2$ tetrahedra and are characterized by having pore openings of uniform dimensions, having a significant ion-exchange capacity and being capable of reversibly desorbing an adsorbed phase which is dispersed throughout the internal voids of the crystal without displacing any atoms which make up the permanent crystal structure.

Other crystalline microporous compositions which are not zeolitic, i.e. do not contain $AlO_2$ tetrahedra as essential framework constituents, but which exhibit the ion-exchange and/or adsorption characteristics of the zeolites are also known. Metal organosilicates which are said to possess ion-exchange properties, have uniform pores and are capable of reversibly adsorbing molecules having molecular diameters of about 6 Å or less, are reported in U.S. Pat. No. 3,941,871 issued Mar. 2, 1976 to Dwyer et al. A pure silica polymorph, silicalite, having molecular sieving properties and a neutral framework containing neither cations nor cation sites is disclosed in U.S. Pat. No. 4,061,724 issued Dec. 6, 1977 to R. W. Grose et al.

A recently reported class of microporous compositions and the first framework oxide molecular sieves synthesized without silica, are the crystalline aluminophosphate compositions disclosed in U.S. Pat. No. 4,310,440 issued Jan. 12, 1982 to Wilson et al. These materials are formed from $AlO_2$ and $PO_2$ tetrahedra and have electrovalently neutral frameworks as in the case of silica polymorphs. Unlike the silica molecular sieve, silicalite, which is hydrophobic due to the absence of extra-structural cations, the aluminophosphate molecular sieves are moderately hydrophilic, apparently due to the difference in electronegativity between aluminum and phosphorus. Their intracrystalline pore volumes and pore diameters are comparable to those known for zeolites and silica molecular sieves.

In copending and commonly assigned application Ser. No. 400,438, filed July 26, 1982, now U.S. Pat. No. 4,440,871, there is described a novel class of silicon-substituted aluminophosphates which are both microporous and crystalline. The materials have a three dimensions crystal framework of $PO_2^+$, $AlO_2^-$ and $SiO_2$ tetrahedral units and, exclusive of any alkali metal or calcium which may optionally be present, an as-synthesized empirical chemical composition on an anhydrous basis of:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3; the maximum value in each case depending upon the molecular dimensions of the templating agent and the available void volume of the pore system of the particular silicoaluminophosphate species involved; and "x", "y", and "z" represent the mole fractions of silicon, aluminum and phosphorus, respectively, present as tetrahedral oxides. The minimum value for each of "x", "y", and "z" is 0.01 and preferably 0.02. The maximum value for "x" is 0.98; for "y" is 0.60; and for "z" is 0.52. These silicoaluminophosphates exhibit several physical and chemical properties which are characteristic of aluminosilicate zeolites and aluminophosphates.

In copending and commonly assigned application Ser. No. 480,738, filed Mar. 31, 1983; now U.S. Pat. No. 4,500,651, there is described a novel class of titanium-containing molecular sieves whose chemical composition in the as-synthesized and anhydrous form is represented by the unit empirical formula:

$$mR:(Ti_xAl_yP_z)O_2$$

wherein "R" represents at least one organic templating agent present in the intracrystalline pore system; "m" represents the moles of "R" present per mole of $(Ti_xAl_yP_z)O_2$ has a value of between zero and about 5.0; and "x", "y" and "z" represent the mole fractions of titanium, aluminum and phosphorus, respectively, present as tetrahedral oxides.

In copending and commonly assigned application Ser. No. 514,334, filed July 15, 1983, now U.S. Pat. No. 4,567,029, there is described a novel class of crystalline metal aluminophosphates having three-dimensional microporous framework structures of $MO_2$, $AlO_2$ and $PO_2$ tetrahedral units and having an empirical chemical composition on an anhydrous basis expressed by the formula:

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3; "M" represents at least one metal of the group magnesium, manganese, zinc and cobalt; and "x", "y" and "z" represent the mole fraction of the metal "M", aluminum and phosphorus, respectively, present as tetrahedral oxides.

In copending and commonly assigned application Ser. No. 514,335, filed July 15, 1983, now U.S. Pat. No. 4,554,143, there is described a novel class of crystalline ferroaluminophosphates having a three-dimensional microporous framework structure of $FeO_2$, $AlO_2$ and $PO_2$ tetrahedral units and having an empirical chemical composition on a anhydrous basis expressed by the formula

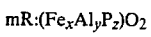

$$mR:(Fe_xAl_yP_z)O_2$$

wherein "R" represents at least one organic templating agent present in the intracrystalline pore system; "m" represents the moles of "R" present per mole of $(Fe_xAl_yP_z)O_2$ and has a value of from zero to 0.3; and "x", "y" and "z" represent the mole fraction of the iron, aluminum and phosphorous, respectively, present as tetrahedral oxides.

The instant invention relates to new molecular sieve compositions having framework tetrahedral oxide units of $TiO_2$, $AlO_2^-$, $PO_2^+$ and $SiO_2$.

SUMMARY OF THE INVENTION

The instant invention relates to a new class of molecular sieves having a three-dimensional microporous crystal framework structures of $TiO_2$, $AlO_2^-$, $PO_2^+$ and $SiO_2$ tetrahedral oxide units. These new titanium-aluminum-phosphorus-silicon-oxide molecular sieves exhibit ion-exchange, adsorbtion and catalytic properties and, accordingly, find wide use as adsorbents and catalysts. The members of this novel class of compositions have crystal framework structures of $TiO_2$, $AlO_2^-$, $PO_2^+$ and $SiO_2$ tetrahedral units and have an empirical chemical composition on an anhydrous basis expressed by the formula:

wherein "R" represents at least one organic templating agent present in the intracrystalline pore system; "m" represents the molar amount of "R" present per mole of $(Ti_wAl_xP_ySi_z)O_2$; and has a value of from zero to about 0.3; and "w", "x", "y" and "z" represent the mole fractions of titanium, aluminum, phosphorus and silicon, respectively present as tetrahedral oxides. The instant molecular sieve compositions are charcterized in several ways as distinct from heretofore known molecular sieves, including the aforementioned ternary compositions. The instant molecular sieves are characterized by the enhanced thermal stability of certain species and by the existence of species heretofore unknown for binary and ternary molecular sieves.

The molecular sieves of the instant invention will be generally referred to by the acronym "TiAPSO" to designate a crystal framework of $TiO_2$, $AlO_2^-$, $PO_2^+$ and $SiO_2$ tetraheral oxide units. Actual class members will be identified as structural species by assigning a number to the species and, accordingly, are identified as "TiAPSO-i" wherein "i" is an integer. This designation is an arbitrary one and is not intended to denote structural relationship to another material(s) which may also be characterized by a numbering system.

DETAILED DESCRIPTION OF THE INVENTION

The instant invention relates to a new class of three-dimensional microporous crystalline molecular sieves having a crystal framework structure of $TiO_2$, $AlO_2^-$, $PO_2^+$ and $SiO_2$ tetrahedral units. These new molecular sieves exhibit ion-exchange, adsorption and catalytic properties, and accordingly, find wide use as adsorbents and catalysts.

Figure 1:
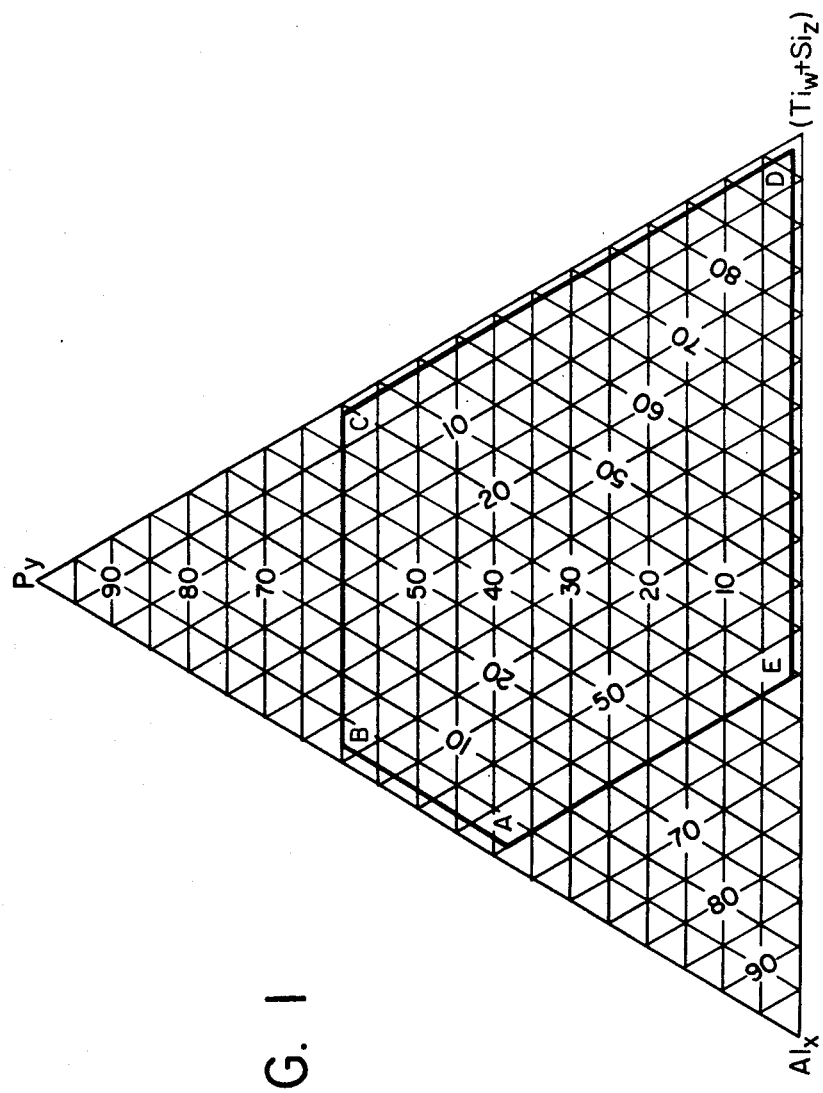
FIG. 1 is a ternary diagram wherein parameters relating to the instant compositions are set forth as mole fractions.

The TiAPSO molecular sieves of the instant invention have three-dimensional microporous framework structures of $TiO_2$, $AlO_2$, $PO_2$ and $SiO_2$ tetrahedral oxide units having an empirical chemical composition on an anhydrous basis expressed by the formula:

wherein "R" represents at least one organic templating agent present in the intracrystalline pore system; "m" represents the molar amount of "R" present per mole of $(Ti_wAl_xP_ySi_z)O_2$ and has a value of from zero to about 0.3; and "w", "x", "y" and "z" represent the mole fractions of titanium, aluminum, phosphorus and silicon, respectively, present as tetrahedral oxides and each has a value of at least 0.01. The mole fractions "w", "x", "y" and "z" are generally defined being within the pentagonal compositional area defined by points A, B, C, D and E of the ternary diagram of FIG. 1. Points A, B, C, D and E of FIG. 1 have the following values for "w", "x", "y", and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

Figure 2:
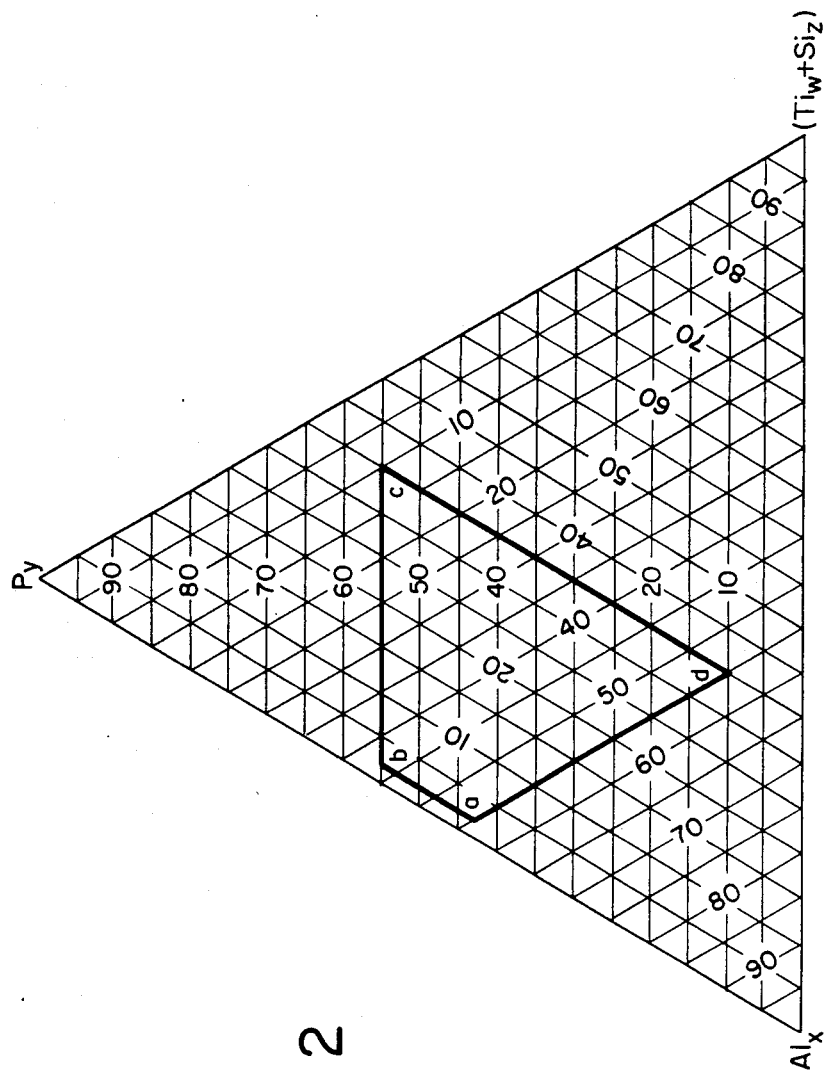
FIG. 2 is a ternary diagram wherein parameters relating to preferred compositions are set forth as mole fractions.

In the preferred subclass of TiAPSO molecular sieves the values "w", "x", "y" and "z" in the above formular are within the tetragonal compositional area defined by points a, b, c and d of the ternary diagram which is FIG. 2 of the drawings, said points a, b, c and d representing the following values for "w", "x", "y" and "z".

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The TiAPSOs of this invention are useful as absorbents, catalysts, ion-exchangers, and the like in much the same fashion as aluminosilicates have been employed heretofore, although their chemical and physical properties are not necessarily similar to those observed for aluminosilicates.

TiAPSO compositions are generally synthesized by hydrothermal crystallization from a reaction mixture containing active resources of titanium silicon, aluminum and phosphorus, and preferably an organic templating, i.e., structure-directing, agent, preferably a compound of an element or Group VA of the Periodic Table, and/or optionally an alkali or metal metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the TiAPSO product are obtained, usually a period of from hours to several weeks. Generally, the crystallization time is from about 2 hours to about 30 days and typically from about 4 hours to about 20 days. The product is recovered by any convenient method such as centrifugation or filtration.

In synthesizing the TiAPSO compositions of the instant invention, it is preferred to employ a reaction mixture composition expressed in terms of the molar ratios as follows:

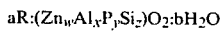

$$aR:(Zn_wAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; and "w", "x", "y" and "z" represent the mole fractions of titanium, aluminum, phosphorus and silicon, respectively, and each has a value of at least 0.01.

Figure 3:
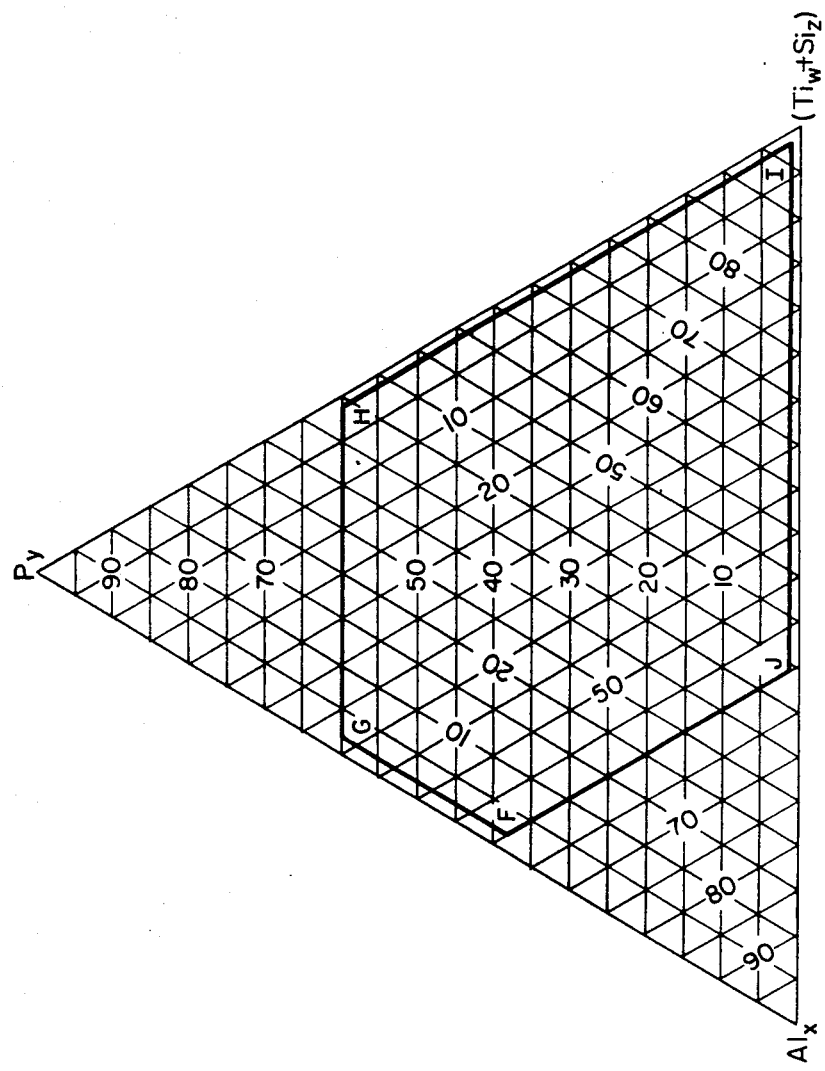
FIG. 3 is a ternary diagram wherein parameters relating to the reaction mixtures employed in the preparation of this compositions of this invention are set forth as mole fractions.

In a preferred embodiment the reaction mixture is selected such that the mole fractions "w", "x", "y" and "z" are generally defined as being within the pentagonal compositional area defined by points E, F, G, H and I of the ternary diagram of FIG. 3. Points E, F, G, H and I of FIG. 3 have the following values for "w", "x", "y" and "z";

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

For reasons unknown at present, not every reaction mixture gave crystalline TiAPSO products when reaction products were examined for TiAPSO products by X-ray analysis. Those reaction mixtures from which crystalline TiAPSO products were obtained are reported in the examples hereinafter as numbered examples with the TiAPSO products identified and those reaction mixtures from which TiAPSO products were not identified by use of X-ray analysis are also reported. In the foregoing expression of the reaction composition, the reactants are normalized with respect to the total of "w", "x", "y" and "z" such that (w+x+y+z)=1.00 mole, whereas in the examples the reaction mixtures are expressed in terms of molar oxide ratios and may be normalized to the moles of $P_2O_5$. This latter form is readily converted to the former form by routine calculations by dividing the number of moles of each component (including the template and water) by the total number of moles of titanium, aluminum, phosphorus and silicon which results in normalized mole fractions based on total moles of the aforementioned components. In forming the reaction mixture from which the instant molecular sieves are formed the organic templating agent can be any of those heretofore proposed for use in the synthesis of conventional zeolite aluminosilicates. In general these compounds contain elements of Group VA of the Periodic Table of Elements, particularly nitrogen, phosphorus, arsenic and antimony, preferably nitrogen or phosphorus and most preferably nitrogen, which compounds also contain at least one alkyl or aryl group having from 1 to 8 carbon atoms. Particularly preferred compounds for use as templating agents are the amines, quaternary phosphonium compounds and quaternary ammonium compounds, the latter two being represented generally by the formula $R_4X^+$ wherein "X" is nitrogen or phosphorus and each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. The mono-, di- and triamines are advantageously utilized, either alone or in combination with a quaternary ammonium compound or other templating compound. Mixtures of two or more templating agents can either produce mixtures of the desired TiAPSOs or the more strongly directing templating species may control the course of the reaction with the other templating agents serving primarily to establish the pH conditions of the reaction gel. Representative templating agents include: tetramethylammonium; tetraethylammonium; tetrapropylammonium; tetrabutylammonium ions; tetrapentylammonium ions; di-n-propylamine; tri-n-propylamine; triethylamine; triethanolamine; piperidine; cyclohexylamine; 2-methylpyridine; N,N-dimethylbenzylamine; N,N-dimethylethanolamine; choline; N,N'-dimethylpiperazine; 1,4-diazabicyclo(2,2,2,)octane; N-methyldiethanolamine, N-methylethanolamine; N-methylpiperidine; 3-methylpiperidine; N-methylcycohexylamine; 3-methylpyridine; 4-methylpyridine; quinculidine; N,N'-dimethyl-1,4-diazabicyclo(2,2,2)octane ion; di-n-butylamine, neopentylamine; di-n-pentylamine; isopropylamine; t-butylamine; ethylenediamine; pyrrolidine; and 2-imidazolidone. Not every templating agent will direct the formation of every species of TiAPSO, i.e., single templating agent can, with proper manipulation of the reaction conditions, direct the formation of several TiAPSO compositions, and a given TiAPSO composition can be produced using several different templating agents.

The source of silicon may be a silica, either as a silica sol or as fumed silica, a reactive solid amorphous precipitated silica, silica gel, alkoxides of silicon, silicic acid or alkali metal silicate and the like; such that the formation of reactive silicon in situ is provided to form $SiO_2$ tetrahedral oxide units.

The most suitable phosphorus source yet found for the present process is phosphoric acid, but organic phosphates such as triethyl phosphate have been found satisfactory, and so also have crystalline or amorphous aluminophosphates such as the $AlPO_4$ composition of U.S. Pat. No. 4,310,440. Organo-phosphorus compounds, such as tetrabutylphosphonium bromide, do not apparently serve as reactive sources of phosphorus, but these compounds do function as templating agents. Conventional phosphorus salts such as sodium metaphosphate, may be used, at least in part, as the phosphorus source, but are not preferred.

The preferred aluminum source is either an aluminum alkoxide, such as aluminum isoproproxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The source of titanium can be introduced into the reaction system in any form which permits the formation in situ of reactive form of titanium, i.e., reactive to form the framework tetrahedral oxide unit $TiO_2$. Compounds of titanium which may be employed include oxides, hydroxides, alkoxides, titanates, titanium chelates, nitrates, sulfates, halides, carboxylates (e.g., acetates) and the like.

While not essential to the synthesis of TiAPSO compositions, stirring or other moderate agitation of the reaction mixture and/or seeding the reaction mixture with seed crystals of either the TiAPSO species to be produced or a topologically similar aluminophosphate, aluminosilicate or molecular sieve composition, facilitates the crystallization procedure.

After crystallization the TiAPSO product may be isolated and advantageously washed with water and dried in air. The as-synthesized TiAPSO generally contains within its internal pore system at least one form of any templating agent, also referred to herein as the "organic moiety", employed in its formation. Most commonly the organic moiety is present, at least in part, as a charge-balancing cation as is generally the case with as-synthesized aluminosilicate zeolites prepared from organic-containing reaction systems. It is possible, however, that some or all of the organic moiety may be an occluded molecular species in a particular TiAPSO species. As a general rule the templating agent, and hence any occluded organic species, is too large to move freely through the pore system of the TiAPSO product and must be removed by calcining the TiAPSO at temperatures of from 200° C. to 700° C. to thermally degrade the organic species. In a few instances the pores of the TiAPSO product are sufficiently large to permit transport of the templating agent, particularly if the latter is a small molecular, and accordingly complete or partial removal thereof can be accomplished by conventional desorption procedures such as carried out in the case of zeolites. It will be understood that the term "as-synthesized" as used herein does not include the condition of the TiAPSO species wherein any organic moiety occupying the intracrystalline pore system as a result of the hydrothermal crystallization process has been reduced by post-synthesis treatment such that the value of "m" in the composition formula $$mR: (Ti_wAl_xP_ySi_z)O_2$$

has a value of less than 0.02. The other symbols of the formula are as defined hereinabove. In those preparations in which an alkoxide is employed as the source of titanium, aluminum, phosphorus or silicon the corresponding alcohol is necessarily present in the reaction mixture since it is a hydrolysis product of the alkoxide. It has not been determined whether this alcohol participates in the synthesis process as a templating agent. For the purposes of this application, however, this alcohol is arbitrarily omitted from the class of templating agents, even if it is present in the as-synthesized TiAPSO compositions.

Since the present TiAPSO compositions are formed from $TiO_2$, $AlO_2$, $PO_2$ and $SiO_2$ tetrahedral units which, respectively, have a net charge of $-2$, $-1$, $+1$ and 0. The matter of cation exchangeability is considerably more complicated than in the case of zeolitic molecular sieves in which, ideally, there is a stoichiometric relationship between $AlO_2^-$ tetrahedra and charge-balancing cations. In the instant compositions, an $AlO_2^-$ tetrahedron can be balanced electrically either by association with a $PO_2^+$ tetrahedron or a simple cation such as an alkali metal cation, a cation of titanium present in the reaction mixture, or an organic cation derived from the templating agent. It has also been postulated that non-adjacent $AlO_2^-$ and $PO_2^+$ tetrahedral pairs can be balanced by $Na^+$ and $OH^-$ respectively [Flanigen and Grose, Molecular Sieve Zeolites-I, ACS, Washington, D.C. (1971)]

The TiAPSO compositions of the present invention may exhibit cation-exchange capacity when analyzed using ion-exchange techniques heretofore employed with zeolitic aluminosilicates and have pore diameters which are inherent in the lattice structure of each species and which are at least about 3 Å in diameter. Ion exchange of TiAPSO compositions is ordinarily possible only after organic moiety derived from the template, present as a result of synthesis, has been removed from the pore system. Dehydration to remove water present in the as-synthesized TiAPSO compositions can usually be accomplished, to some degree at least, in the usual manner without removal of the organic moiety, but the absence of the organic species greatly facilitates adsorption and desorption procedures. As illustrated hereinafter, the TiAPSO materials have various degrees of hydrothermal and thermal stability, some being quite remarkable in this regard, and function well as molecular sieve adsorbents and hydrocarbon conversion catalysts or catalyst bases.

In each example the stainless steel reaction vessel utilized was lined with the inert plastic material, polytetrafluoroethylene, to avoid contamination of the reaction mixture. In general, the final reaction mixture from which each TiAPSO composition is crystallized is prepared by forming mixtures of less than all of the reagents and thereafter incorporating into these mixtures addition reagents either singly or in the form of other intermediate mixtures of two or more reagents. In some instance the reagents admixed retain their identity in the intermediate mixture and in other cases some or all of the reagents are involved in chemical reactions to produce new reagents. The term "mixture" is applied in both cases. Further, unless otherwise specified, each intermediate mixture as well as the final reaction mixture was stirred until substantially homogeneous.

X-ray analysis of reaction products are obtained by X-ray analysis using standard X-ray powder diffraction techniques. The radiation source is a high-intensity, copper target, X-ray tube operated at 50 Kv and 40 ma. The diffraction pattern from the copper K-alpha radiation and graphite monochromator is suitably recorded by an X-ray spectrometer scintillation counter, pulse height analyzer and strip chart recorder. Flat compressed powder samples are scanned at 2° (2 theta) per minute, using a two second time constant. Interplanar spacings (d) in Angstrom units are obtained from the position of the diffraction peaks expressed as $2\theta$ where $\theta$ is the Bragg angle as observed on the strip chart. Intensities are determined from the heights of diffraction peaks after subtracting background, "$I_o$" being the intensity of the strongest line or peak, and "I" being the intensity of each of the other peaks. Alternatively, the X-ray patterns are obtained from the copper K-alpha radiation by use of computer based techniques using Siemens D-500 X-ray powder diffractometers, Siemens Type K-805 X-ray sources, available from Siemens Corporation, Cherry Hill, N.J., with appropriate computer interface.

As will be understood by those skilled in the art the determination of the parameter 2 theta is subject to both human and mechanical error, which in combination, can impose an uncertainty of about ±0.4 on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m, w and vw which represent very strong, strong, medium, weak and very weak, respectively.

In certain instances the purity of a synthesized product is assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The molecular sieves of the instant invention may be characterized by their x-ray powder diffraction patterns and such may have one of the x-ray patterns set forth in the following Tables A through V, wherein said x-ray patterns are for both the as-synthesized and calcined forms unless otherwise noted:

TABLE A

| | (TiAPSO—5) | |
|---|---|---|
| 2θ | d (Å) | Relative Intensity |
| 7.3–7.5 | 12.11–11.79 | s–vs |
| 19.7–19.9 | 4.51–4.46 | m |
| 20.9–21.0 | 4.25–4.23 | m–s |
| 22.3–22.5 | 3.99–3.95 | m–vs |
| 25.8–26.1 | 3.453–3.411 | m |
| 28.9–29.1 | 3.089–3.069 | w–m |

TABLE B

| | (TiAPSO—11) | |
|---|---|---|
| 2θ | d (Å) | Relative Intensity |
| 9.4–9.6 | 9.41–9.21 | vw–m |
| 19.9–20.5 | 4.46–4.33 | m |
| 21.0–21.8 | 4.23–4.08 | vs |
| 22.0–22.1 | 4.04–4.02 | m–vs |
| 22.4–22.6 | 3.97–3.93 | m–s |
| 22.7 | 3.92 | m |
| 23.1–23.4 | 3.85–3.80 | m–vs |

TABLE C

| | (TiAPSO—16) | |
|---|---|---|
| 2θ | d (Å) | Relative Intensity |
| 11.4 | 7.75 | m–vs |
| 18.7 | 4.75 | m |
| 21.9–22.1 | 4.05–4.02 | m–vs |
| 26.4–26.5 | 3.370–3.363 | m |
| 29.6–29.8 | 3.018–3.002 | m |
| 29.9 | 2.984 | m |
| 30.1 | 2.971 | m |

TABLE D

| | (TiAPSO—34) | |
|---|---|---|
| 2θ | d (Å) | Relative Intensity |
| 9.4–9.5 | 9.41–9.31 | vs |
| 12.9–13.0 | 6.86–6.81 | w–m |
| 16.0–16.2 | 5.54–5.47 | w–m |
| 20.5–20.8 | 4.33–4.27 | m–vs |
| 30.5–30.9 | 2.931–2.894 | m |

TABLE D-continued

| | (TiAPSO—34) | |
|---|---|---|
| 2θ | d (Å) | Relative Intensity |
| 31.5–31.6 | 2.840–2.831 | vw–m |

TABLE E

| | (TiAPSO—35) | |
|---|---|---|
| 2θ | d (Å) | Relative Intensity |
| 10.9–11.1 | 8.12–7.97 | m |
| 13.3–13.7 | 6.66–6.46 | m |
| 17.3–17.4 | 5.13–5.10 | w–m |
| 20.8–21.1 | 4.27–4.21 | m |
| 21.9–22.2 | 4.06–4.00 | m–vs |
| 28.3–28.7 | 3.153–3.110 | m |

TABLE F

| | (TiAPSO—44) | |
|---|---|---|
| 2θ | d (Å) | Relative Intensity |
| 9.5 | 9.30 | s |
| 16.1 | 5.49 | m |
| 20.8 | 4.27 | vs |
| 22.0 | 4.05 | m |
| 24.5 | 3.63 | m |
| 30.9 | 2.893 | m |

The following examples are provided to further illustrate the invention and are not intended to be limiting thereof:

PREPARATIVE REAGENTS

In the following examples the TiAPSO compositions were prepared using numerous regents. The reagents employed and abbreviations employed herein, if any, for such reagents are as follows:

(a) Al ipro: aluminum isopropoxide;
(b) LUDOX-LS: LUDOX-LS is the tradename of DuPont for an aqueous solution of 30 weight percent $SiO_2$ and 0.1 weight percent $Na_2O$;
(c) $H_3PO_4$: 85 weight percent aqueous phosphoric acid;
(d) Ti ipro: titanium isopropoxide;
(e) TEAOH: 40 weight percent aqueous solution of tetraethylammonium hydroxide;
(f) $Pr_2NH$: di-n-propylamine, $(C_3H_7)_2NH$.
(g) $Pr_3NH$: tri-n-propylamine, $(C_3H_7)_3N$;
(h) Quin: Quinuclidine, $(C_7H_{13}N)$;
(i) MQuin: Methyl Quinuclidine hydroxide, $(C_7H_{13}NCH_3OH)$; and
(j) C-hex: cyclohexylamine.

PREPARATIVE PROCEDURES

The following preparative examples were carried out by forming a starting reaction mixture by adding the $H_3PO_4$ and the water. This mixture was mixed and to this mixture the aluminum isoproxide was added. This mixture was then blended until a homogeneous mixture was observed. To this mixture the LUDOX-LS was added and the resulting mixture blended (about 2 minutes) until a homogeneous mixture was observed.

The titanium isopropoxide was added to the above mixture and the resulting mixture blended until a homogeneous mixture was observed. The organic templating agent was then added to the resulting mixture and the resulting mixture blended until a homogeneous mixture was observed, i.e., about 2 to 4 minutes. When the organic templating agent was quinuclidine the procedure was modified such that the quinuclidine was dissolved in about one half the water and accordingly the H₃PO₄ was mixed with about one half the water. (The pH of the mixture was measured and adjusted for temperature). The mixture was than placed in a lined (polytetrafluoroethylene) stainless steel pressure vessel and digested at a temperature (150° C. or 200° C.) for a time or placed in line screw top bottles for digestion at 100° C. All digestions were carried out at the autogeneous pressure.

The molar composition for each preparation will be given by the relative moles of the components of the reaction mixture. H₃PO₄ and titanium isopropoxide are given respectively in terms of the P₂O₅ and TiO₂ content of the reaction mixture.

All digestions were carried out at the autogeneous pressure. The products were removed from the reaction vessel cooled and evaluated as set forth hereinafter.

EXAMPLES 1 TO 30

TiAPSO molecular sieves were prepared according to the above described preparative procedure and the TiAPSO products determined by x-ray analysis. The results of examples 1 to 30 are set forth in Tables I and II.

TABLE I

| Example | Template[1] | Temp (°C.) | Time (days) | TiAPSO Product(s)[2] |
|---|---|---|---|---|
| 1 | Quin | 150 | 28 | TiAPSO—16 |
| 2 | Quin | 200 | 10 | TiAPSO—35; TiAPSO—16 |
| 3 | Quin | 200 | 28 | TiAPSO—35; TiAPSO—16 |
| 4 | Quin | 225 | 5 | TiAPSO—16 |
| 5 | Pr₃N | 150 | 3 | TiAPSO—5 |
| 6 | Pr₃N | 150 | 11 | TiAPSO—5 |
| 7 | Pr₃N | 200 | 3 | TiAPSO—5 |
| 8 | Pr₃N | 200 | 11 | TiAPSO—5 |
| 9 | Pr₃N | 100 | 3 | — |
| 10 | Pr₃N | 100 | 11 | — |

[1]Reaction mixture comprised: 1.0 R : 0.2 TiO₂:0.9 Al₂O₃:0.9 P₂O₅:0.2 SiO₂:50 H₂O where "R" is the organic template.
[2]Major species as identified by x-ray powder diffraction pattern of product, except that when two or more species were identified the species are listed in the order of their predomenance in the product. The "—" denotes that TiAPSO products were not identified by X-ray analysis.

TABLE II

| Example | Template[1] | Temp (°C.) | Time (days) | TiAPSO Product(s)[2] |
|---|---|---|---|---|
| 11 | C—hex | 225 | 5 | TiAPSO—44; TiAPSO—35 |
| 12 | Pr₂NH | 150 | 4 | TiAPSO—11; TiAPSO—41 |
| 13 | Pr₂NH | 150 | 11 | TiAPSO—11 |
| 14 | Pr₂NH | 200 | 4 | TiAPSO—11 |
| 15 | PR₂NH | 200 | 11 | TiAPSO—11 |
| 16 | Pr₂NH | 100 | 4 | — |
| 17 | Pr₂NH | 100 | 11 | — |
| 18 | TEAOH | 150 | 4 | TiAPSO—34; TiAPSO—5 |
| 19 | TEAOH | 150 | 10 | TiAPSO—34; TiAPSO—5 |
| 20 | TEAOH | 200 | 4 | TiAPSO—5; TiAPSO—34 |
| 21 | TEAOH | 200 | 10 | TiAPSO—5; TiAPSO—34 |
| 22 | TEAOH | 100 | 17 | — |
| 23 | TEAOH | 150 | 2 | TiAPSO—34; TiAPSO—5 |
| 24 | TEAOH | 150 | 13 | TiAPSO—34 |
| 25 | TEAOH | 200 | 2 | TiAPSO—34; TiAPSO—5 |
| 26 | TEAOH | 200 | 13 | TiAPSO—34 |
| 27 | MQuin | 150 | 21 | — |
| 28 | MQuin | 200 | 21 | TiAPSO—35 |
| 29 | MQuin | 150 | 45 | TiAPSO—35 |
| 30 | MQuin | 200 | 45 | TiAPSO—35 |

[1]The reaction mixture generally comprised: kR:0.2 TiO₂:0.9 Al₂O₃:p P₂O₅:q SiO₂:50 H₂O where R is the organic template; "k" is 1.0 for examples 11 to 22 and 27 to 30 and is 1.5 for examples 23 to 26; "p" is 0.9 for examples 12-30 and is 1.0 for example 11; and "q" is 0.6 for examples 11 and 23-26 and is 0.2 for examples 12-22 and 27-30.
[2]Major species as identified by x-ray powder diffraction pattern of product, except that when two or more species were identified the species are listed in the order of their predominance in the product. The "—" denotes that TiAPSO products were not identified by X-ray analysis.

EXAMPLE 31

Samples of the products of examples 4, 6, 15, 24 and 30 were subjected to chemical analysis. The chemical analysis for each product is given hereinafter with the example in which the TiAPSO was prepared being given in parenthesis after the designation of the TiAPSO species.

(a) The chemical analysis for TiAPSO-16 (Example 4) was:

| Component | Weight Percent |
|---|---|
| Al₂O₃ | 27.1 |
| P₂O₅ | 36.1 |
| TiO₂ | 6.8 |
| SiO₂ | 6.7 |
| Carbon | 12.0 |
| Nitrogen | 1.9 |
| LOI* | 22.9 |

*LOI = Loss on Ignition

The above chemical analysis gives an overall product composition in molar oxide ratios (anhydrous basis) of: 0.085 TiO₂:0.266 Al₂O₃:0.254 P₂O₅:0.112 SiO₂; and a formula (anhydrous basis) of:

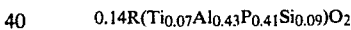

0.14R(Ti₀.₀₇Al₀.₄₃P₀.₄₁Si₀.₀₉)O₂

(b) The chemical analysis for TiAPSO-35 (Example 30) was:

| Component | Weight Percent |
|---|---|
| Al₂O₃ | 23.4 |
| P₂O₅ | 28.3 |
| TiO₂ | 17.6 |
| SiO₂ | 4.37 |
| Carbon | 11.3 |
| Nitrogen | 1.6 |
| LOI* | 26.3 |

*LOI = Loss on Ignition

The above chemical analysis gives an overal product composition in molar oxide ratios (anhydrous basis) of: 0.220 TiO₂:0.230 Al₂O₃:0.199 P₂O₅:0.073 SiO₂; and a formula (anhydrous basis) of:

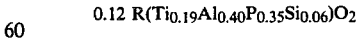

0.12 R(Ti₀.₁₉Al₀.₄₀P₀.₃₅Si₀.₀₆)O₂

(c) The chemical analysis for TiAPSO-5 (Example 6) was:

| Component | Weight Percent |
|---|---|
| Al₂O₃ | 34.0 |
| P₂O₅ | 46.9 |
| TiO₂ | 3.0 |

-continued

| Component | Weight Percent |
|---|---|
| SiO$_2$ | 1.2 |
| Carbon | 5.8 |
| Nitrogen | 0.74 |
| LOI* | 14.4 |

*LOI = Loss on Ignition

The above chemical analysis gives an overall product composition in molar oxide ratios (anhydrous basis) of: 0.038 TiO$_2$:0.334 Al$_2$O$_3$:0.330 P$_2$O$_5$:0.020 SiO$_2$; and a formula (anhydrous basis) of:

0.054R(Ti$_{0.03}$Al$_{0.48}$P$_{0.48}$Si$_{0.01}$)O$_2$ (d) The chemical analysis of TiAPSO-11 (Example 15) was:

| Component | Weight Percent |
|---|---|
| Al$_2$O$_3$ | 35.8 |
| P$_2$O$_5$ | 49.0 |
| TiO$_2$ | 1.08 |
| SiO$_2$ | 3.3 |
| Carbon | 5.0 |
| Nitrogen | 1.0 |
| LOI* | 10.5 |

*LOI = Loss on Ignition

The above chemical analysis gives an overall product composition in molar oxide ratios (anhydrous basis) of: 0.014 TiO$_2$:0.351 Al$_2$O$_3$:0.345 P$_2$O$_5$:0.055 SiO$_2$; and a formula (anhydrous basis) of:

0.07R(Ti$_{0.01}$Al$_{0.48}$P$_{0.47}$Si$_{0.04}$)O$_2$ (e) The chemical analysis for TiAPSO-34 (example 24) was:

| Component | Weight Percent |
|---|---|
| Al$_2$O$_3$ | 32.3 |
| P$_2$O$_5$ | 37.9 |
| TiO$_2$ | 0.4 |
| SiO$_2$ | 8.2 |
| Carbon | 9.8 |
| Nitrogen | 1.6 |
| LOI* | 20.5 |

*LOI = Loss on Ignition

The above chemical analysis gives an overall product composition in molar oxide ratios (anhydrous basis) of: 0.01 TiO$_2$:0.32 Al$_2$O$_3$:0.27 P$_2$O$_5$:0.14 SiO$_2$; and a formula (anhydrous basis) of:

0.103R(Ti$_{0.01}$Al$_{0.48}$P$_{0.41}$Si$_{0.11}$)O$_2$

EXAMPLE 32

EDAX (energy dispersive analysis by x-ray) microprobe analysis in conjunction with SEM (scanning electron microscope was carried out on clear crystals from the products of example 4, 11, 12, and 21. Analysis of crystals having a morphology characteristic of TiAPSO compositions gave the following analysis based on relative peak heights:
(a) TiAPSO-44/35 (Example 11):

| | Average of Spot Probes |
|---|---|
| Ti | 0.02 |
| Al | 0.97 |
| P | 0.94 |
| Si | 0.25 |

(b) TiAPSO-16 (Example 4):

| | Average of Spot Probes |
|---|---|
| Ti | 0.38 |
| Al | 0.79 |
| P | 0.84 |
| Si | 0.33 |

(c) TiAPSO-34/5 (Example 21):

| | Average of Spot Probes |
|---|---|
| Ti | 0.005 |
| Al | 0.85 |
| P | 1.00 |
| Si | 0.08 |

(d) TiAPSO-11 (Example 12):

| | Average of Spot Probes |
|---|---|
| Ti | 0.12 |
| Al | 0.88 |
| P | 0.84 |
| Si | 0.07 |

EXAMPLE 33

Samples of the TiAPSO products of Examples 4, 13 and 6 were evaluated for adsorption capacities in the calcined form by calcination in air to remove at least part of the organic templating agent, as hereinafter set forth. The adsorption capacities of each calcined sample were measured using a standard McBain-Bakr gravimetric adsorption apparatus. The samples were activated in a vacuum at 350° C. prior to measurement. The McBain-Bakr data for the aforementioned calcined TiAPSO products were:
(a) TiAPSO-16 (Example 4):

| Adsorbate | Kinetic Diameter, Å | Pressure (Torr) | Temp (°C.) | Wt. %* Adsorbed |
|---|---|---|---|---|
| O$_2$ | 3.46 | 102 | −183 | 3.3 |
| O$_2$ | 3.46 | 744 | −183 | 12.8** |
| n-hexane | 4.3 | 95 | 23.6 | 7.0 |
| H$_2$O | 2.65 | 4.6 | 23.3 | 13.4 |
| H$_2$O | 2.65 | 19 | 23.2 | 25.4 |

*TiAPSO—16 was calcined at 500° C. in air for 1.5 hours prior to being activated.
**Sample may not have been fully equilibrated.

The above data demonstrate that the pore size of the calcined product is about 4.3 Å.
(b) TiAPSO-11 (Example 13):

| Adsorbate | Kinetic Diameter, Å | Pressure (Torr) | Temp (°C.) | Wt. %* Adsorbed |
|---|---|---|---|---|
| O$_2$ | 3.46 | 101 | −183 | 9.3 |
| O$_2$ | 3.46 | 736 | −183 | 10.3 |
| neopentane | 5.0 | 742 | 23.0 | 1.1 |
| cyclohexane | 6.0 | 67 | 22.9 | 5.2 |
| H$_2$O | 2.65 | 4.6 | 22.4 | 12.4 |

-continued

| Adsorbate | Kinetic Diameter, Å | Pressure (Torr) | Temp (°C.) | Wt. %* Adsorbed |
|---|---|---|---|---|
| H₂O | 2.65 | 19 | 22.5 | 23.4 |

*TiAPSO—11 was calcined at 600° C. in air for 1.5 hours prior to being activated.

The above data demonstrate that the pore size of the calcined product is about 6.0 Å.

(c) TiAPSO-5 (Example 6):

| Adsorbate | Kinetic Diameter, Å | Pressure (Torr) | Temp (°C.) | Wt. %* Adsorbed |
|---|---|---|---|---|
| O₂ | 3.46 | 101 | −183 | 13.0 |
| O₂ | 3.46 | 736 | −183 | 14.5 |
| neopentane | 6.2 | 742 | 23.0 | 4.9 |
| cyclohexane | 6.0 | 67 | 22.9 | 7.1 |
| H₂O | 2.65 | 4.6 | 22.4 | 14.7 |
| H₂O | 2.65 | 19 | 22.5 | 23.4 |

*TiAPSO was calcined at 600° C. in air for 2.5 hours prior to being activated.

The above data demonstrate that the pore size of the calcined product is greater than 6.2 Å.

EXAMPLE 34

(a) TiAPSO-5 compositions, as referred to herein in both the as-synthesized and calcined forms, have a characteristic x-ray powder diffraction pattern which contains at least the d-spacings set forth in Table III below:

TABLE III

| 2θ | d, (Å) | Relative Intensity |
|---|---|---|
| 7.3–7.5 | 12.11–11.79 | s–vs |
| 19.7–19.9 | 4.51–4.46 | m |
| 20.9–21.0 | 4.25–4.23 | m–s |
| 22.3–22.5 | 3.99–3.95 | m–vs |
| 25.8–26.1 | 3.453–3.411 | m |
| 28.9–29.1 | 3.089–3.069 | w–m |

(b) TiAPSO-5 compositions for which x-ray powder diffraction data have been obtained to date have patterns which are X-ray powder diffraction patterns characterized by Table IV below.

TABLE IV

| 2θ | d, (Å) | 100 × I/Io |
|---|---|---|
| 7.3–7.5 | 12.11–11.79 | 94–100 |
| 12.9–13.0 | 6.86–6.81 | 19–22 |
| 14.9–15.0 | 5.95–5.91 | 9–21 |
| 19.7–19.9 | 4.51–4.46 | 26–50 |
| 20.9–21.0 | 4.25–4.23 | 43–82 |
| 22.3–22.5 | 3.99–3.95 | 60–100 |
| 24.6–24.8 | 3.62–3.59 | 7–9 |
| 25.8–26.1 | 3.453–3.414 | 25–40 |
| 28.9–29.1 | 3.089–3.069 | 17–27 |
| 30.0–30.2 | 2.979–2.959 | 18–25 |
| 33.5–33.7 | 2.675–2.660 | 6–9 |
| 34.5–34.7 | 2.600–2.585 | 17–19 |
| 36.8–37.1 | 2.442–2.423 | 6 |
| 37.5–37.8 | 2.398–2.380 | 10–13 |
| 41.4–41.5 | 2.181–2.176 | 5–6 |
| 41.7–42.0 | 2.166–2.151 | 3–4 |
| 42.5–42.9 | 2.127–2.108 | 3–6 |
| 43.6–43.7 | 2.076–2.071 | 3–4 |
| 44.9–45.0 | 2.019–2.014 | 3–4 |
| 47.4–47.6 | 1.918–1.910 | 5–7 |
| 47.8–47.9 | 1.903–1.900 | 6–7 |
| 51.4–51.5 | 1.778–1.774 | 4–5 |
| 51.8–51.9 | 1.765–1.762 | 3–4 |
| 55.6 | 1.653 | 6 |

(c) A portion of the as-synthesized TiAPSO-5 of Example 6 was subjected to X-ray analysis. The TiAPSO-5 product was characterized by the x-ray powder diffraction pattern of Table V, below:

TABLE V

| 2θ | d, (Å) | 100 × I/Io |
|---|---|---|
| 7.3 | 12.11 | 94 |
| 9.1* | 9.72 | 3 |
| 12.9 | 6.86 | 19 |
| 13.6* | 6.51 | 6 |
| 14.9 | 5.95 | 21 |
| 18.2* | 4.87 | 6 |
| 19.7 | 4.51 | 50 |
| 20.9 | 4.25 | 82 |
| 22.3 | 3.99 | 100 |
| 24.6 | 3.62 | 9 |
| 25.8 | 3.453 | 40 |
| 28.9 | 3.089 | 27 |
| 30.0 | 2.979 | 25 |
| 33.5 | 2.675 | 9 |
| 34.5 | 2.600 | 19 |
| 36.8 | 2.442 | 6 |
| 37.5 | 2.398 | 13 |
| 41.4 | 2.181 | 6 |
| 42.0 | 2.151 | 4 |
| 42.5 | 2.127 | 6 |
| 43.6 | 2.076 | 4 |
| 44.9 | 2.019 | 3 |
| 47.6 | 1.910 | 7 |
| 51.4 | 1.778 | 4 |
| 51.8 | 1.765 | 4 |
| 55.6 | 1.653 | 6 |

*peak may contain an impurity.

(d) The TiAPSO-5 compositions of Example 6 was calcined at 600° C. in air for 2.5 hours. The calcined product was characterized by the x-ray powder diffraction pattern shown in Table VI, below:

TABLE VI

| 2θ | d, (Å) | 100 × I/Io |
|---|---|---|
| 7.5 | 11.79 | 100 |
| 12.5* | 7.08 | 8 |
| 13.0 | 6.81 | 22 |
| 15.0 | 5.91 | 9 |
| 19.9 | 4.46 | 26 |
| 21.0 | 4.23 | 43 |
| 22.5 | 3.95 | 60 |
| 24.8 | 3.59 | 7 |
| 26.1 | 3.414 | 25 |
| 29.1 | 3.069 | 17 |
| 30.2 | 2.959 | 18 |
| 33.7 | 2.660 | 6 |
| 34.7 | 2.585 | 17 |
| 37.1 | 2.423 | 6 |
| 37.8 | 2.380 | 10 |
| 41.7 | 2.166 | 3 |
| 42.9 | 2.108 | 3 |
| 47.4 | 1.918 | 5 |
| 47.9 | 1.900 | 6 |
| 51.4 | 1.778 | 3 |
| 51.8 | 1.765 | 3 |

*peak may contain an impurity.

EXAMPLE 35

(a) TiAPSO-11, as referred to herein in both the as-synthesied and calcined forms, have a characteristic x-ray powder diffraction pattern which contains at least the d-spacings set forth in Table VII below:

TABLE VII

| 2θ | d, (Å) | Relative Intensity |
|---|---|---|
| 9.4–9.6 | 9.41–9.21 | vw–m |
| 19.9–20.5 | 4.46–4.33 | m |
| 21.0–21.8 | 4.23–4.08 | vs |
| 22.0–22.1 | 4.04–4.02 | m–vs |
| 22.4–22.6 | 3.97–3.93 | m–s |
| 22.7 | 3.92 | m |

TABLE VII-continued

| 2θ | d, (Å) | Relative Intensity |
|---|---|---|
| 23.1–23.4 | 3.85–3.80 | m–vs |

(b) The TiAPSO-11 compositions for which x-ray powder diffraction data have been obtained to date have patterns which are characterized by the x-ray powder diffraction pattern of Table VIII below:

TABLE VIII

| 2θ | d, (Å) | 100 × I/Io |
|---|---|---|
| 8.0–8.1 | 11.05–10.92 | 23–59 |
| 9.4–9.6 | 9.41–9.21 | sh–73 |
| 9.8 | 9.03 | 51 |
| 12.8–13.2 | 6.92–6.71 | 26–27 |
| 13.5–13.7 | 6.56–6.46 | 9–11 |
| 14.7–15.0 | 6.03–5.91 | 9–18 |
| 15.6–16.1 | 5.68–5.51 | 32–63 |
| 16.2–16.3 | 5.47–5.44 | 7–18 |
| 19.0–19.5 | 4.67–4.55 | 20–23 |
| 19.9–20.5 | 4.46–4.33 | 31–68 |
| 21.0–21.8 | 4.23–4.08 | 100 |
| 22.0–22.1 | 4.04–4.02 | 57–100 |
| 22.4–22.6 | 3.97–3.93 | 54–82 |
| 22.7 | 3.92 | 73 |
| 23.1–23.4 | 3.85–3.80 | 63–91 |
| 23.9–24.4 | 3.72–3.65 | 23 |
| 24.7 | 3.60 | 27 |
| 26.5–26.6 | 3.363–3.351 | 17–36 |
| 27.2–27.3 | 3.278–3.267 | 16–20 |
| 27.6–27.7 | 3.232–3.220 | 20–23 |
| 27.8–27.9 | 3.209–3.200 | 20–21 |
| 28.5–28.6 | 3.132–3.121 | 14–27 |
| 28.7 | 3.110 | 11–32 |
| 29.0–29.5 | 3.079–3.028 | 27–31 |
| 29.6–29.7 | 3.018–3.008 | 23–34 |
| 30.3–30.4 | 2.950–2.940 | 20–22 |
| 31.4–31.6 | 2.849–2.831 | 14–23 |
| 32.5–32.9 | 2.755–2.722 | 26–32 |
| 33.9–34.2 | 2.644–2.622 | 11–23 |
| 35.5–35.6 | 2.529–2.522 | 17–19 |
| 36.5 | 2.462 | 18 |
| 37.2–37.5 | 2.417–2.398 | 14–23 |
| 38.7–39.4 | 2.327–2.287 | 14–17 |
| 41.0 | 2.201 | 11 |
| 42.8 | 2.113 | 14 |
| 43.6 | 2.076 | 9 |
| 44.5–44.6 | 2.036–2.032 | 9–14 |
| 45.0 | 2.014 | 14 |
| 48.7–49.2 | 1.870–18.52 | 14 |
| 49.4 | 1.845 | 11 |
| 49.6 | 1.838 | 11 |
| 50.6 | 1.804 | 7–18 |
| 53.4 | 1.716 | 11 |
| 53.6 | 1.707 | 9 |
| 54.6–54.7 | 1.681–1.678 | 9–14 |
| 55.4–55.8 | 1.658–1.647 | 11–14 |

(c) A portion of the as-synthesized TiAPSO-11 of Example was subjected to x-ray analysis. The TiAPSO-11 product was characterized by the x-ray powder diffraction pattern of Table IX, below:

TABLE IX

| 2θ | d, (Å) | 100 × I/Io |
|---|---|---|
| 8.1 | 10.92 | 59 |
| 9.4 | 9.41 | 73 |
| 13.2 | 6.71 | 27 |
| 15.0 | 5.91 | 18 |
| 15.7 | 5.64 | 50 |
| 16.3 | 5.44 | 18 |
| 19.0 | 4.67 | 23 |
| 20.5 | 4.33 | 68 |
| 21.0 | 4.23 | 100 |
| 22.1 | 4.02 | 73 |
| 22.6 | 3.93 | 82 |
| 22.7 | 3.92 | 73 |
| 23.2 | 3.83 | 91 |
| 24.4 | 3.65 | 23 |
| 24.7 | 3.60 | 27 |
| 26.5 | 3.363 | 36 |
| 28.5 | 3.132 | 27 |
| 28.7 | 3.110 | 32 |
| 29.0 | 3.079 | 27 |
| 29.5 | 3.028 | 23 |
| 31.4 | 2.849 | 23 |
| 32.9 | 2.722 | 32 |
| 34.2 | 2.622 | 23 |
| 36.5 | 2.462 | 18 |
| 37.5 | 2.398 | 23 |
| 39.4 | 2.287 | 14 |
| 42.8 | 2.113 | 14 |
| 44.6 | 2.032 | 14 |
| 45.0 | 2.014 | 14 |
| 48.7 | 1.870 | 14 |
| 50.6 | 1.804 | 18 |
| 54.7 | 1.678 | 14 |
| 55.4 | 1.658 | 14 |

(d) The TiAPSO-11 composition of Example 13 was calcined at 500° C. in air for 2 hours. The calcined product was characterized by the x-ray powder diffraction pattern shown in Table X, below:

TABLE X

| 2θ | d, (Å) | 100 × I/Io |
|---|---|---|
| 8.1 | 10.92 | 23 |
| 9.6 | 9.21 | sh |
| 9.8 | 9.03 | 51 |
| 12.8 | 6.92 | 26 |
| 13.5 | 6.56 | 11 |
| 13.7 | 6.46 | 9 |
| 14.7 | 6.03 | 9 |
| 16.1 | 5.51 | 63 |
| 19.5 | 4.55 | 20 |
| 19.9 | 4.46 | 31 |
| 21.8 | 4.08 | 100 |
| 22.1 | 4.02 | 57 |
| 22.4 | 3.97 | 54 |
| 23.4 | 3.80 | 63 |
| 23.9 | 3.72 | 23 |
| 24.2 | 3.68 | 17 |
| 26.6 | 3.351 | 17 |
| 27.2 | 3.278 | 20 |
| 27.6 | 3.232 | 23 |
| 27.8 | 3.209 | 20 |
| 28.5 | 3.132 | 14 |
| 28.7 | 3.110 | 11 |
| 29.5 | 3.028 | 31 |
| 29.7 | 3.008 | 34 |
| 30.3 | 2.950 | 20 |
| 31.6 | 2.831 | 14 |
| 32.5 | 2.755 | 26 |
| 33.9 | 2.644 | 11 |
| 35.5 | 2.529 | 17 |
| 37.2 | 2.417 | 14 |
| 38.7 | 2.327 | 17 |
| 41.0 | 2.201 | 11 |
| 43.6 | 2.076 | 9 |
| 44.5 | 2.036 | 9 |
| 49.2 | 1.852 | 14 |
| 49.4 | 1.845 | 11 |
| 49.6 | 1.838 | 11 |
| 53.4 | 1.716 | 9 |
| 53.6 | 1.707 | 9 |
| 55.8 | 1.647 | 11 |

EXAMPLE 36

(a) TiAPSO-16, as referred to herein in both the as-synthesized and calcined form, have a characteristic x-ray powder diffraction pattern which contains at least the d-spacings set forth in Table XI below:

TABLE XI

| 2θ | d, (Å) | Relative Intensity |
|---|---|---|
| 11.4 | 7.75 | m-vs |
| 18.7 | 4.75 | m |
| 21.9-22.1 | 4.05-4.02 | m-vs |
| 26.4-26.5 | 3.370-3.363 | m |
| 29.6-29.8 | 3.018-3.002 | m |
| 29.9 | 2.984 | m |
| 30.1 | 2.971 | m |

(b) The TiAPSO-16 compositions for which x-ray powder diffraction data have been obtained to date have patterns which are characterized by the X-ray powder diffraction pattern of Table XII below:

TABLE XII

| 2θ | d, (Å) | 100 × I/Io |
|---|---|---|
| 10.5 | 8.41 | 5 |
| 11.4 | 7.75 | 72-100 |
| 18.7 | 4.75 | 25-59 |
| 21.1 | 4.21 | 3 |
| 21.9-22.1 | 4.05-4.02 | 56-100 |
| 22.8-22.9 | 3.90-3.89 | 10-15 |
| 23.3 | 3.818 | 3 |
| 25.0 | 3.561 | 6 |
| 25.4-25.5 | 3.506-3.489 | 13-17 |
| 26.4-26.5 | 3.370-3.363 | 20-23 |
| 26.6 | 3.346 | 16 |
| 26.9-27.1 | 3.314-3.290 | 4-15 |
| 28.9-29.1 | 3.088-3.073 | 12-13 |
| 29.6-29.8 | 3.018-3.002 | 22-27 |
| 29.9 | 2.984 | 24 |
| 30.1 | 2.971 | 23 |
| 32.5-32.7 | 2.755-2.739 | 3-4 |
| 34.4-34.8 | 2.607-2.581 | 3-5 |
| 37.3-37.6 | 2.411-2.394 | 4-5 |
| 37.8-37.9 | 2.380-2.373 | 8-14 |
| 38.2-38.4 | 2.356-2.343 | 5 |
| 39.5 | 2.282 | 3-4 |
| 39.7-39.8 | 2.270-2.265 | 3-5 |
| 40.1 | 2.247 | 7 |
| 40.5 | 2.227 | 4 |
| 44.4 | 2.040 | 3 |
| 47.8-47.9 | 1.904-1.899 | 5 |
| 48.0-48.1 | 1.897-1.893 | 6-8 |
| 48.2-48.3 | 1.887-1.855 | 7-8 |
| 48.4-48.5 | 1.881-1.876 | 7-8 |
| 48.8 | 1.865 | 5-6 |
| 49.0 | 1.858 | 5 |
| 49.2 | 1.853 | 4 |
| 54.2 | 1.692 | 3 |
| 54.3 | 1.689 | 3 |

(c) A portion of the as-synthesized TiAPSO-16 of example 4 was subjected to x-ray analysis. The TiAPSO-16 product was characterized by the x-ray powder diffraction pattern of Table XIII, below:

TABLE XIII

| 2θ | d, (Å) | 100 × I/Io |
|---|---|---|
| 11.4 | 7.75 | 72 |
| 18.7 | 4.74 | 59 |
| 22.1 | 4.02 | 100 |
| 22.9 | 3.89 | 11 |
| 25.3 | 3.521 | 15 |
| 26.4 | 3.376 | 13 |
| 26.6 | 3.346 | 16 |
| 26.9 | 3.314 | 15 |
| 29.1 | 3.073 | 13 |
| 29.8 | 3.002 | 22 |
| 29.9 | 2.984 | 24 |
| 30.1 | 2.971 | 23 |
| 34.8 | 2.581 | 3 |
| 37.6 | 2.395 | 5 |
| 37.9 | 2.371 | 14 |
| 38.4 | 2.343 | 5 |
| 39.5 | 2.282 | 4 |
| 39.7 | 2.270 | 5 |

TABLE XIII-continued

| 2θ | d, (Å) | 100 × I/Io |
|---|---|---|
| 40.1 | 2.247 | 7 |
| 40.5 | 2.227 | 4 |
| 47.8 | 1.904 | 5 |
| 48.1 | 1.893 | 8 |
| 48.2 | 1.887 | 8 |
| 48.5 | 1.876 | 8 |
| 48.8 | 1.865 | 6 |
| 49.0 | 1.858 | 5 |
| 49.2 | 1.853 | 4 |

*peak may contain impurity (d) The TiAPSO-16 composition of part (c) was calcined at 500° C. in air for 1.5 hours. The calcined product was characterized by the x-ray powder diffraction pattern shown in Table XIV, below:

TABLE XIV

| 2θ | d, (Å) | 100 × I/Io |
|---|---|---|
| 10.5 | 8.41 | 5 |
| 11.4 | 7.75 | 100 |
| 18.7 | 4.75 | 25 |
| 21.1 | 4.27 | 3 |
| 21.9 | 4.05 | 56 |
| 22.8 | 3.90 | 10 |
| 25.0 | 3.561 | 6 |
| 25.4* | 3.506 | 14 |
| 25.5 | 3.489 | 13 |
| 26.4 | 3.370 | 20 |
| 28.9 | 3.088 | 12 |
| 29.7 | 3.007 | 27 |
| 34.6 | 2.594 | 5 |
| 37.6 | 2.391 | 5 |
| 37.9 | 2.373 | 9 |
| 38.2 | 2.356 | 5 |
| 48.0 | 1.897 | 6 |
| 48.3 | 1.885 | 7 |

*peak may contain impurity

EXAMPLE 37

(a) TiAPSO-34, as referred to herein in both the as-synthesized and calcined forms, have a characteristic x-ray powder diffraction pattern which contains at least the d-spacings set forth in Table XV below:

TABLE XV

| 2θ | d, (Å) | Relative Intensity |
|---|---|---|
| 9.4-9.5 | 9.41-9.31 | vs |
| 12.9-13.0 | 6.86-6.81 | w-m |
| 16.0-16.2 | 5.54-5.47 | w-m |
| 20.5-20.8 | 4.33-4.27 | m-vs |
| 30.5-30.9 | 2.931-2.894 | m |
| 31.5-31.6 | 2.840-2.831 | vw-m |

(b) The TiAPSO-34 compositions for which x-ray powder diffraction data have been obtained to date have patterns which are characterized by the x-ray powder diffraction pattern of Table XVI below:

TABLE XVI

| 2θ | d, (Å) | 100 × I/Io |
|---|---|---|
| 9.4-9.5 | 9.41-9.31 | 100 |
| 12.9-13.0 | 6.86-6.81 | 16-31 |
| 14.0-14.1 | 6.33-6.28 | 7-16 |
| 16.0-16.2 | 5.54-5.47 | 19-50 |
| 17.8-17.9 | 4.98-4.96 | 16-23 |
| 19.2 | 4.62 | 10 |
| 20.5-20.8 | 4.33-4.27 | 38-97 |
| 22.1-22.2 | 4.02-4.00 | 8-9 |
| 23.1-23.3 | 3.85-3.82 | 8-14 |
| 25.0-25.1 | 3.562-3.548 | 17-27 |
| 25.8-26.2 | 3.453-3.401 | 19-21 |
| 27.5-27.9 | 3.243-3.198 | 7-10 |

TABLE XVI-continued

| 2θ | d, (Å) | 100 × I/Io |
|---|---|---|
| 28.2–28.3 | 3.164–3.153 | 7–12 |
| 29.5–29.8 | 3.028–2.998 | 8–12 |
| 30.5–30.9 | 2.931–2.894 | 31–39 |
| 31.1–31.3 | 2.876–2.858 | Sh–29 |
| 31.5–31.6 | 2.840–2.831 | 8–32 |
| 32.3–32.4 | 2.772–2.763 | 6–7 |
| 33.2 | 2.698 | 5 |
| 33.8 | 2.652 | 5 |
| 34.4–34.9 | 2.607–2.571 | 8–9 |
| 35.0 | 2.564 | 3 |
| 36.1–36.2 | 2.488–2.481 | 6–7 |
| 38.8 | 2.321 | 3 |
| 39.6–39.8 | 2.276–2.265 | 5–7 |
| 40.2 | 2.243 | 5 |
| 43.0 | 2.103 | 5 |
| 43.4 | 2.085 | 7 |
| 47.5 | 1.914 | 5 |
| 48.9–49.2 | 1.863–1.852 | 5–8 |
| 49.8 | 1.831 | 5 |
| 50.9–51.0 | 1.794–1.791 | 7–8 |
| 51.5–51.6 | 1.774–1.771 | 3–5 |
| 53.1–53.2 | 1.725–1.722 | 7–8 |
| 54.4–54.5 | 1.687–1.684 | 5–6 |
| 55.8–55.9 | 1.647–1.645 | 6–7 |

(c) A portion of the as-synthesized TiAPSO-34 of example 24 was subjected to x-ray analysis. The TiAPSO-34 product was characterized by the x-ray powder diffraction pattern of Table XVII below:

TABLE XVII

| 2θ | d, (Å) | 100 × I/Io |
|---|---|---|
| 9.4 | 9.41 | 100 |
| 12.9 | 6.86 | 16 |
| 14.0 | 6.33 | 16 |
| 16.0 | 5.54 | 50 |
| 17.9 | 4.96 | 23 |
| 20.5 | 4.33 | 97 |
| 22.1 | 4.02 | 8 |
| 23.1 | 3.85 | 8 |
| 25.1 | 3.548 | 27 |
| 25.8 | 3.453 | 21 |
| 27.5 | 3.243 | 7 |
| 28.3 | 3.153 | 7 |
| 29.5 | 3.028 | 8 |
| 30.5 | 2.931 | 39 |
| 31.1 | 2.876 | 29 |
| 31.6 | 2.831 | 8 |
| 32.4 | 2.763 | 7 |
| 33.2 | 2.698 | 5 |
| 33.8 | 2.652 | 5 |
| 34.4 | 2.607 | 8 |
| 35.0 | 2.564 | 3 |
| 36.2 | 2.481 | 7 |
| 38.8 | 2.321 | 3 |
| 39.6 | 2.276 | 7 |
| 43.0 | 2.103 | 5 |
| 43.4 | 2.085 | 7 |
| 47.5 | 1.914 | 5 |
| 48.9 | 1.863 | 8 |
| 49.8 | 1.831 | 5 |
| 50.9 | 1.794 | 7 |
| 51.6 | 1.771 | 3 |
| 53.1 | 1.725 | 7 |
| 54.4 | 1.687 | 5 |
| 55.8 | 1.647 | 7 |

(d) The TiAPSO-34 compositions of example 24 was calcined at 500° C. in air for 2 hours. The calcined product was characterized by the x-ray powder diffraction pattern shown in Table XVIII, below:

TABLE XVIII

| 2θ | d, (Å) | 100 × I/Io |
|---|---|---|
| 9.5 | 9.31 | 100 |
| 13.0 | 6.81 | 31 |
| 14.1 | 6.28 | 7 |
| 16.2 | 5.47 | 19 |
| 17.9 | 4.96 | 16 |
| 19.2 | 4.62 | 10 |
| 20.8 | 4.27 | 38 |
| 22.2 | 4.00 | 9 |
| 23.3 | 3.82 | 14 |
| 25.0 | 3.562 | 17 |
| 26.2 | 3.401 | 19 |
| 27.9 | 3.198 | 10 |
| 28.2 | 3.164 | 12 |
| 29.8 | 2.998 | 12 |
| 30.9 | 2.894 | 31 |
| 31.3 | 2.858 | sh |
| 32.4 | 2.763 | 9 |
| 34.9 | 2.571 | 9 |
| 36.2 | 2.481 | 7 |
| 39.8 | 2.265 | 5 |
| 40.2 | 2.243 | 5 |
| 49.2 | 1.852 | 5 |
| 51.0 | 1.791 | 7 |

EXAMPLE 38

(a) TiAPSO-35, as referred to herein in both the as-synthesized and calcined forms, have a characteristic x-ray powder diffraction pattern which contains at least the d-spacings set forth in Table XIX below:

TABLE XIX

| 2θ | d, (Å) | Relative Intensity |
|---|---|---|
| 10.9–11.1 | 8.12–7.97 | m |
| 13.3–13.7 | 6.66–6.46 | m |
| 17.3–17.4 | 5.13–5.10 | w–m |
| 20.8–21.1 | 4.27–4.21 | m |
| 21.9–22.2 | 4.06–4.00 | m–vs |
| 28.3–28.7 | 3.153–3.110 | m |

(b) The TiAPSO-35 compositions for which x-ray powder diffraction data have been obtained to date have patterns which are characterized by the x-ray powder diffraction pattern of Table XX below:

TABLE XX

| 2θ | d, (Å) | 100 × I/Io |
|---|---|---|
| 8.6–8.8 | 10.28–10.05 | 13–14 |
| 10.9–11.1 | 8.12–7.97 | 36–74 |
| 13.3–13.7 | 6.66–6.46 | 20–39 |
| 15.9–16.1 | 5.57–5.51 | 11–15 |
| 17.3–17.4 | 5.13–5.10 | 17–75 |
| 17.6–17.7 | 5.04–5.01 | 13–17 |
| 20.8–21.1 | 4.27–4.21 | 25–49 |
| 21.9–22.2 | 4.06–4.00 | 65–100 |
| 23.2–23.7 | 3.83–3.75 | 22–32 |
| 24.9–25.2 | 3.58–3.534 | 19–30 |
| 26.6–26.9 | 3.363–3.314 | 19–35 |
| 28.3–28.7 | 3.153–3.110 | 30–48 |
| 29.1–29.2 | 3.069–3.058 | 11–15 |
| 29.6–29.7 | 3.018–3.008 | 6–39 |
| 31.5–31.7 | 2.840–2.823 | 9–11 |
| 32.1–32.7 | 2.788–2.739 | 30–41 |
| 34.3–34.6 | 2.614–2.592 | 11–17 |
| 35.0–35.1 | 2.564–2.557 | 4–5 |
| 35.8–35.9 | 2.508–2.501 | 5–6 |
| 37.8–38.0 | 2.380–2.368 | 9–13 |
| 39.5 | 2.281 | 4–5 |
| 40.9 | 2.206 | 3–4 |
| 41.9 | 2.156 | 6 |
| 42.1–42.6 | 2.146–2.122 | 5–6 |
| 42.7 | 2.118 | 4–6 |
| 48.4–48.5 | 1.881–1.877 | 9–13 |
| 49.0 | 1.859 | 5–6 |
| 50.1 | 1.821 | 10–11 |
| 55.0–55.1 | 1.670–1.667 | 9–13 |

TABLE XX-continued

| 2θ | d, (Å) | 100 × I/Io |
|---|---|---|
| 55.4–55.5 | 1.658–1.656 | 9–10 |

(c) A portion of the as-synthesized TiAPSO-35 of example 30 was subjected to x-ray analysis. The TiAPSO-35 product was characterized by the x-ray powder diffraction pattern of Table XXI below:

TABLE XXI

| 2θ | d, (Å) | 100 × I/Io |
|---|---|---|
| 8.6 | 10.28 | 13 |
| 10.9 | 8.12 | 36 |
| 11.4* | 7.76 | 6 |
| 13.3 | 6.66 | 21 |
| 15.9 | 5.57 | 11 |
| 17.3 | 5.13 | 75 |
| 17.7 | 5.01 | 13 |
| 18.6* | 4.77 | 6 |
| 20.8 | 4.27 | 49 |
| 21.9 | 4.06 | 100 |
| 22.6* | 3.93 | 9 |
| 23.2 | 3.83 | 32 |
| 24.9 | 3.58 | 19 |
| 25.2* | 3.534 | 28 |
| 26.9 | 3.314 | 19 |
| 28.3 | 3.153 | 47 |
| 29.1 | 3.069 | 11 |
| 29.7 | 3.008 | 6 |
| 31.5 | 2.840 | 9 |
| 32.1 | 2.788 | 38 |
| 34.3 | 2.614 | 11 |
| 35.0 | 2.564 | 4 |
| 35.9 | 2.501 | 6 |
| 37.8 | 2.380 | 9 |
| 39.5 | 2.281 | 4 |
| 40.9 | 2.206 | 4 |
| 41.9 | 2.156 | 6 |
| 42.6 | 2.122 | 6 |
| 42.7 | 2.118 | 6 |
| 44.7* | 2.027 | 6 |
| 47.6* | 1.910 | 11 |
| 48.4 | 1.881 | 9 |
| 49.0 | 1.859 | 6 |
| 49.6* | 1.838 | 7 |
| 50.1 | 1.821 | 11 |
| 54.0* | 1.698 | 6 |
| 55.0 | 1.670 | 9 |
| 55.4 | 1.658 | 9 |

*peak may contain an impurity (d) The calcined TiAPSO-35 compositions of example 2 was calcined at 600° C. in air for 2 hours. The calcined product was characterized by the x-ray powder diffraction pattern shown in Table XXII, below.

TABLE XXII

| 2θ | d, (Å) | 100 × I/Io |
|---|---|---|
| 8.8 | 10.05 | 13 |
| 11.1 | 7.97 | 74 |
| 11.5* | 7.69 | 100 |
| 13.7 | 6.46 | 39 |
| 17.6 | 5.04 | 17 |
| 18.9* | 4.70 | 26 |
| 21.1 | 4.21 | 26 |
| 22.2 | 4.00 | 65 |
| 23.1* | 3.85 | 26 |
| 23.7 | 3.75 | 22 |
| 25.2 | 3.534 | 30 |
| 26.6 | 3.363 | 35 |
| 27.4* | 3.255 | 26 |
| 28.7 | 3.110 | 35 |
| 29.6* | 3.018 | 39 |
| 29.8* | 2.998 | 44 |
| 32.7 | 2.739 | 30 |
| 34.6 | 2.592 | 17 |
| 38.0 | 2.368 | 13 |
| 48.5 | 1.877 | 13 |

TABLE XXII-continued

| 2θ | d, (Å) | 100 × I/Io |
|---|---|---|
| 55.1 | 1.667 | 13 |

*peak may contain an impurity

EXAMPLE 39

(a) TiAPSO-44, as referred to herein in both the as-synthesized and calcined forms, have a characteristic x-ray powder diffraction pattern which contains at least the d-spacings set forth in Table XXIII below:

TABLE XIX

| 2θ | d, (Å) | Relative Intensity |
|---|---|---|
| 9.5 | 9.30 | s |
| 16.1 | 5.49 | m |
| 20.8 | 4.27 | vs |
| 22.0 | 4.05 | m |
| 24.5 | 3.63 | m |
| 30.9 | 2.893 | m |

(b) The TiAPSO-44 compositions for which x-ray powder diffraction data have been obtained to date have patterns which are characterized by the x-ray powder diffraction pattern of Table XXIV below:

TABLE XXIV

| 2θ | d, (Å) | 100 × I/Io |
|---|---|---|
| 9.5 | 9.30 | 83 |
| 11.0 | 8.06 | 45 |
| 13.0 | 6.79 | 24 |
| 13.4 | 6.62 | 30 |
| 13.9 | 6.40 | 3 |
| 16.1 | 5.49 | 51 |
| 17.4 | 5.11 | 48 |
| 19.0 | 4.66 | 5 |
| 20.8 | 4.27 | 100 |
| 21.1 | 4.22 | 36 |
| 22.0 | 4.05 | 77 |
| 22.7 | 3.92 | 7 |
| 23.2 | 3.83 | 19 |
| 24.5 | 3.63 | 52 |
| 26.2 | 3.400 | 20 |
| 27.0 | 3.307 | 11 |
| 27.9 | 3.195 | 10 |
| 28.6 | 3.123 | 28 |
| 29.8 | 3.000 | 6 |
| 30.3 | 2.954 | 14 |
| 30.9 | 2.893 | 57 |
| 31.7 | 2.820 | 6 |
| 32.2 | 2.777 | 30 |
| 32.6 | 2.745 | 5 |
| 33.1 | 2.708 | 4 |
| 35.0 | 2.567 | 4 |
| 35.7 | 2.519 | 11 |
| 38.7 | 2.328 | 3 |
| 42.1 | 2.145 | 4 |
| 42.6 | 2.122 | 5 |
| 43.7 | 2.073 | 4 |
| 47.4 | 1.920 | 3 |
| 48.2 | 1.888 | 12 |
| 48.8 | 1.867 | 8 |
| 51.5 | 1.775 | 6 |
| 54.1 | 1.696 | 7 |

(c) A portion of the as-synthesized TiAPSO-44 of Example 11 was subjected to X-ray analysis. The TiAPSO-44 product was characterized by the x-ray powder diffraction pattern of Table XXV, below:

TABLE XXV

| 2θ | d, (Å) | 100 × I/Io |
|---|---|---|
| 8.7* | 10.21 | 14 |
| 9.5 | 9.30 | 83 |
| 11.0 | 8.06 | 45 |

TABLE XXV-continued

| 2θ | d, (Å) | 100 × I/Io |
|---|---|---|
| 11.7* | 7.57 | 3 |
| 13.0 | 6.79 | 24 |
| 13.4 | 6.62 | 30 |
| 13.9 | 6.40 | 3 |
| 16.1 | 5.49 | 51 |
| 17.4 | 5.11 | 48 |
| 17.8* | 4.98 | 7 |
| 19.0 | 4.66 | 5 |
| 20.8 | 4.27 | 100 |
| 21.1 | 4.22 | 36 |
| 21.5* | 4.13 | 19 |
| 22.0 | 4.05 | 77 |
| 22.7 | 3.92 | 7 |
| 23.2 | 3.83 | 19 |
| 23.6* | 3.78 | 3 |
| 24.5 | 3.63 | 52 |
| 25.1* | 3.554 | 8 |
| 25.4* | 3.501 | 4 |
| 25.6* | 3.481 | 3 |
| 26.2 | 3.400 | 20 |
| 27.0 | 3.307 | 11 |
| 27.9 | 3.195 | 10 |
| 28.6 | 3.123 | 28 |
| 29.2* | 3.062 | 5 |
| 29.8 | 3.000 | 6 |
| 30.3 | 2.954 | 14 |
| 30.9 | 2.893 | 57 |
| 31.7 | 2.820 | 6 |
| 32.2 | 2.777 | 30 |
| 32.6 | 2.745 | 5 |
| 33.1 | 2.708 | 4 |
| 34.6* | 2.595 | 7 |
| 35.0 | 2.567 | 4 |
| 35.1* | 2.559 | 3 |
| 35.7 | 2.519 | 11 |
| 37.9* | 2.372 | 3 |
| 38.7 | 2.328 | 3 |
| 42.1 | 2.145 | 4 |
| 42.4* | 2.134 | 5 |
| 42.6 | 2.122 | 5 |
| 43.0* | 2.103 | 6 |
| 43.7 | 2.073 | 4 |
| 47.4 | 1.920 | 3 |
| 48.2 | 1.888 | 12 |
| 48.7* | 1.871 | 8 |
| 48.8 | 1.867 | 8 |
| 49.7* | 1.836 | 4 |
| 50.4 | 1.809 | 9 |
| 51.5 | 1.775 | 6 |
| 54.1 | 1.696 | 7 |

*peak may contain an impurity

EXAMPLE 40

In order to demonstrate the catalytic activity of the TiAPSO compositions, calcined samples of the TiAPSO products of Examples 6, 13, and 24 were tested for catalytic cracking of n-butane.

The reactor was a cylindrical quartz tube 254 mm. in length and 10.3 mm. I.D. In each test the reactor was loaded with particles of the test TiAPSO which were 20-40 mesh (U.S. std.) in size and in an amount of from 0.5 to 5 grams, the quantity being selected so that the conversion of n-butane was at least 5% and not more than 90% under the test conditions. The TiAPSO samples were calcined in air (TiAPSO-5 at 600° C. for 2.5 hours; TiAPSO-11 at 600° C. for 1.5 hours; and TiAPSO-34 at 500° C. for 2 hours) to remove organic materials from the pore system, and were activated in situ in the reactor in a flowing stream of helium at 500° C. for one hour. The feedstock was a helium-n-butane mixture containing 2 mole percent n-butane and was passed through the reactor at a rate of 50 cc./minute. Analysis of the feedstock and the reactor effluent were carried out using conventional gas chromotography techniques. The reactor effluent was analyzed after 10 minutes of on-stream operation. The pseudo-first-order rate constant ($K_A$) was calculated to determine the relative catalytic activity of the Ti-APSO compositions. The $K_A$ value (cm$^3$/g min) obtained for the TiAPSO compositions are set forth, below, in Table XXVI:

TABLE XXVI

| TiAPSO | $k_A$ |
|---|---|
| TiAPSO—5 | 0.6 |
| TiAPSO—11 | 0.5 |
| TiAPSO—34 | 1.3 |

PROCESS APPLICATIONS

The TiAPSO compositions of the present invention are, in general, hydrophilic and adsorb water preferentially over common hydrocarbon molecules such as paraffins, olefins and aromatic species, e.g., benzene, xylenes and cumene. Thus, the TiAPSOs as a class are useful as desiccants in such adsorption separation/purification processes as natural gas drying, cracked gas drying. Water is also preferentially adsorbed over the so-called permanent gases such as carbon dioxide, nitrogen, oxygen and hydrogen. These TiAPSOs are therefore suitably employed in the drying of reformer hydrogen streams and in the drying of oxygen, nitrogen or air prior to liquifaction.

The present TiAPSO compositions also exhibit novel surface selectivity characteristics which render them useful as catalyst or catalyst bases in a number of hydrocarbon conversion and oxidative combustion reactions. They can be impregnated or otherwise loaded with catalytically active metals by methods well known in the art and used, for example, in fabricating catalysts compositions having silica or alumina bases. Of the general class, those species having pores larger than about 4 Å are preferred for catalytic applications.

Among the hydrocarbon conversion reactions catalyzed by TiAPSO compositions are cracking, hydrocracking, alkylation for both the aromatic and isoparaffin types, isomerization including xylene isomerization, polymerization, reforming, hydrogenation, dehydrogenation, transalkylation, dealkylation, hydrodecyclization and dehydrocyclization.

Using TiAPSO catalyst compositions which contain a hydrogenation promoter such as platinum or palladium, heavy petroleum residual stocks, cyclic stocks and other hydrocrackable charge stocks can be hydrocracked at temperatures in the range of 400° F. to 825° F. using molar ratios of hydrogen to hydrocarbon in the range of between 2 and 80, pressures between 10 and 3500 p.s.i.g., and a liquid hourly space velocity (LHSV) of from 0.1 to 20, preferably 1.0 to 10.

The TiAPSO catalyst compositions employed in hydrocracking are also suitable for use in reforming processes in which the hydrocarbon feedstocks contact the catalyst at temperatures of from about 700° F. to 1000° F., hydrogen pressures of from 100 to 500 p.s.i.g., LHSV values in the range of 0.1 to 10 and hydrogen to hydrocarbon molar ratios in the range of 1 to 20, preferably between 4 and 12.

These same catalysts, i.e. those containing hydrogenation promoters, are also useful in hydroisomerizations processes in which feedstocks such a normal paraffins are converted to saturated branched chain isomers. Hydroisomerization is carried out at a temperature of from about 200° F. to 600° F., preferably 300° F. to 550°

F. with an LHSV value of from about 0.2 to 1.0. Hydrogen is supplied to the reactor in admixture with the hydrocarbon feedstock in molar proportions (hydrogen to hydrocarbon) of between 1 and 5.

At somewhat higher temperatures, i.e. from about 650° F. to 1000° F., preferably 850° F. to 950° F. and usually at somewhat lower pressures within the range of about 15 to 50 p.s.i.g., the same catalyst compositions are used to hydroisomerize normal paraffins. Preferably the paraffin feedstock comprises normal paraffins having a carbon number range of $C_7-C_{20}$. Contact time between the feedstock and the catalyst is generally relatively short to avoid undesireable side reactions such as olefin polymerization and paraffin cracking. LHSV values in the range of 0.1 to 10, preferably 1.0 to 6.0 are suitable.

The unique crystal structure of the present TiAPSO catalysts and their availability in a form totally void of alkali metal content favor their use in the conversion of alkylaromatic compounds, particularly the catalytic disproportionation of toluene, ethylene, trimethyl benzenes, tetramethyl benzenes and the like. In the disproportionation process, isomerization and transalkylation can also occur. Group VIII noble metal adjuvants alone or in conjunction with Group VI-B metals such as tungsten, molybdenum and chromium are preferably included in the catalyst composition in amounts of from about 3 to 15 weight-% of the overall composition. Extraneous hydrogen can, but need not, be present in the reaction zone which is maintained at a temperature of from about 400° to 750° F., pressures in the range of 100 to 2000 p.s.i.g. and LHSV values in the range of 0.1 to 15.

Catalytic cracking processes are preferably carried out with TiAPSO compositions using feedstocks such as gas oils, heavy naphthas, deasphalted crude oil residua, etc., with gasoline being the principal desired product. Temperature conditions of 850° to 1100° F., LHSV values of 0.5 to 10 and pressure conditions of from about 0 to 50 p.s.i.g. are suitable.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the TiAPSO catalyst in conjunction with a Group VIII non-noble metal cation such as titanium and nickel.

In catalytic dealkylation wherein it is desired to cleave paraffinic side chains from aromatic nuclei without substantially hydrogenating the ring structure, relatively high temperatures in the range of about 800°–1000° F. are employed at moderate hydrogen pressures of about 300–1000 p.s.i.g., other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils, deasphalted crude oil residua and the like any of which may contain up to about 5 weight-percent of sulfur and up to about 3 weight-percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constituents markedly inhibits the activity of catalysts of hydrocracking. Consequently, it is necessary to operate at more extreme conditions when it is desired to obtain the same degree of hydrocracking conversion per pass on a relatively nitrogenous feed than are required with a feed containing less organonitrogen compounds. Consequently, the conditions under which denitrogenation, desulfurization and/or hydrocracking can be most expeditiously accomplished in any given situation are necessarily determined in view of the characteristics of the feedstocks in particular the concentration of organonitrogen compounds in the feedstock. As a result of the effect of organonitrogen compounds on the hydrocracking activity of these compositions it is not at all unlikely that the conditions most suitable for denitrogenation of a given feedstock having a relatively high organonitrogen content with minimal hydrocracking, e.g., less than 20 volume percent of fresh feed per pass, might be the same as those preferred for hydrocracking another feedstock having a lower concentration of hydrocracking inhibiting constituents e.g., organonitrogen compounds. Consequently, it has become the practice in this art to establish the conditions under which a certain feed is to be contacted on the basis of preliminary screening tests with the specific catalyst and feedstock.

Isomerization reactions are carried out under conditions similar to those described above for reforming, using somewhat more acidic catalysts. Olefins are preferably isomerized at temperatures of 500°–900° F., while paraffins, naphthenes and alkyl aromatics are isomerized at temperatures of 700°–1000° F. Particularly desirable isomerization reactions contemplated herein include the conversion of n-heptene and/or octane to isoheptanes, iso-octanes, butane to iso-butane, methylcyclopentane to cyclohexane, meta-xylene and/or ortho-xylene to paraxylene, 1-butene to 2-butene and/or isobutene, n-hexene to isohexene, cyclohexene to methylcyclopentene etc. The preferred form of the catalyst is a combination of the TiAPSO with polyvalent metal compounds (such as sulfides) of metals of Group II-A, Group II-B and rare earth metals. For alkylation and dealkylation processes the TiAPSO compositions having pores of at least 5 Å are preferred. When employed for dealkylation of alkyl aromatics, the temperature is usually at least 350° F. and ranges up to a temperature at which substantial cracking of the feedstock or conversion products occurs, generally up to about 700° F. The temperature is preferably at least 450° F. and not greater than the critical temperature of the compound undergoing deakylation. Pressure conditions are applied to retain at least the aromatic feed in the liquid state. For alkylation the temperature can be as low as 250° F. but is preferably at least 350° F. In the alkylation of benzene, toluene and xylene, the preferred alkylating agents are olefins such as ethylene and propylene.

We claim:

1. Crystalline molecular sieves having three-dimensional microporous framework structures of $TiO_2$, $AlO_2$, $PO_2$ and $SiO_2$ tetrahedral units having an empirical chemical composition on an anhydrous basis expressed by the formula:

$$mR: (Ti_wAl_xP_ySi_z)O_2$$

wherein "R" represents at least one organic templating agent present in the intracrystalline pore system; "m" represents the molar amount of "R" present per mole of $(Ti_wAl_xP_ySi_z)O_2$ and has a value of zero (0) to about 0.3; and "w", "x", "y" and "z" represent the mole fractions of titanium, aluminum, phosphorus and silicon respectively, present as tetrahedral oxides, said mole fractions being such that they are within the pentagonal compositional area defined by points A, B, C, D and E of FIG. 1, said crystalline molecular sieves having a characteristic X-ray powder diffraction pattern which contains at least the d-spacings set forth in one of Tables A to F herein.

2. Molecular sieves according to claim 1 wherein the mole fractions of titanium, aluminum, phosphorus and silicon present as tetrahedral oxides are within the tetragonal compositional area defined by points a, b, c and d of FIG. 2.

3. The crystalline molecular sieves of claims 1 or 2 having a characteristic x-ray powder diffraction pattern which contains at least the d-spacings set forth in Table A.

4. The crystalline molecular sieves of claims 1 or 2 having a characteristic x-ray powder diffraction pattern which contains at least the d-spacings set forth in Table B.

5. The crystalline molecular sieves of claims 1 or 2 having a characteristic x-ray powder diffraction pattern which contains at least the d-spacings set forth in Table C.

6. The crystalline molecular sieves of claims 1 or 2 having a characteristic x-ray powder diffraction pattern which contains at least the d-spacings set forth in Table D.

7. The crystalline molecular sieves of claims 1 or 2 having a characteristic x-ray powder diffraction pattern which contains at least the d-spacings set forth in Table E.

8. The crystalline molecular sieves of claims 1 or 2 having a characteristic x-ray powder diffraction pattern which contains at least the d-spacings set forth in Table F.

9. Process for preparing the crystalline molecular sieves of claim 1 having three-dimensional microporous framework structures wherein said process comprises providing a reaction mixture composition for an effective time at an effective temperature sufficient to produce the molecular sieves of claim 1, said composition being expressed in terms of molar oxide ratios as follows:

$$(Ti_wAl_xP_ySi_z)O_2:bH_2O$$

wherein "R" is an organic templating agent: "a" is the amount of "R" and is an effective amount greater than zero to about 6: "b" has a value of from zero to 500; and "w", "x", "y" and "z" represent the mole fractions, respectively, of titanium, aluminum, phosphorus and silicon in the $(Ti_wAl_xP_ySi_z)O_2$ constituent, and each has a value of at least 0.01.

10. Process of claim 9 wherein "w", "x", "y" and "z" are within the pentagonal area defined by points F, G, H, I and J of FIG. 3.

11. Process according to claim 9 wherein the source of phosphorus in the reaction mixture is orthophosphoric acid.

12. Process according to claim 9 wherein the source of phosphorus in the reaction mixture is othrphosphoric acid and the source of aluminum is at least one compound selected from the group consisting of pseudoboehmite and aluminum alkoxide.

13. Process according to claim 12 wherein the aluminum alkoxide is aluminum isopropoxide.

14. Process according to claim 12 wherein the source of silicon is silica.

15. Process according to claim 12 wherein the source of titanium is titanium acetate.

16. Process according to claims 9 or 10 wherein the organic templating agent is a quaternary ammonium or quaternary phosphonium compound having the formula $$R_4X^+$$

wherein X is nitrogen or phosphorus and each R is an alkyl or aryl group containing from 1 to 8 carbon atoms.

17. Process according to claim 9 wherein the organic templating agent is an amine.

18. Process according to claim 9 wherein the templating agent is selected from the group consisting of tetrapropylammonium ion; tetraethylammonium ion; tripropylamine; triethylamine; triethanolamine; piperidine; cyclohexylamine; 2-methyl pyridine; N,N-dimethylbenzylamine; N,N-dimethylethanolamine; choline; N,N-dimethylpiperazine; 1,4-diaziabicyclo-(2,2,2) octane; N-methyldiethanolamine; N-methylethanolamine; N-methylpiperidine; 3-methylpiperidine; N-methylcyclohexylamine; 3-methylpyridine; 4-methylpyridine; quinculidine; N,N'-dimethyl-1,4-diazabicyclo (2,2,2) octane ion; tetramethylammonium ion; tetrabutylammonium ion; tetrapentylammonium ion; di-n-butylamine; neopentylamine; di-n-pentylamine; isopropylamine; t-butylamine; ethylenediamine; pyrrolidine; 2-imidazolidone; di-n-propylamine; and a polymeric quaternary ammonium salt $[(C_{14}H_{32}N_2)(OH)_2]_x$ wherein x is a value of at least 2.

19. Crystalline molecular sieve prepared by calcining the composition of claim 1 or claim 2 said calcination being at a temperature sufficiently high to remove at least some of the organic templating agent present in the intracrystalline pore system.

20. The crystalline molecular sieves of claims 1 or 2 wherein the values of "w" and "z" have the following mole fraction values: "w" is $\geq 0.01$; and "z" is $\geq 0.04$.

21. The process of claim 9 wherein "b" has a value of from about 2 to about 500.

22. The process of claim 21 wherein "b" has a value of from about 2 to about 300.

23. Crystalline molecular sieves having three-dimensional microporous framework structures of $TiO_2$, $AlO_2$, $PO_2$ and $SiO_2$ tetrahedral units having an empirical chemical composition on an anhydrous basis expressed by the formula:

$$mR: (Ti_wAl_xP_ySi_z)O_2$$

wherein "R" represents at least one organic templating agent present in the intracrystalline pore system; "m" represents the molar amount of "R" present per mole of $(Ti_wAl_xP_ySi_z)O_2$ and has a value of zero (0) to about 0.3; and "w", "x", "y" and "z" represent the mole fractions of titanium, aluminum, phosphorus and silicon respectively, present as tetrahedral oxides, said mole fractions being such that they are within the pentagonal compositional area defined by points A, B, C, D and E of FIG. 1 and each has a value of at least 0.01.

24. Molecular sieves according to claim 23 wherein the mole fractions of titanium, aluminum, phosphorus and silicon present as tetrahedral oxides are within the tetragonal compositional area defined by points a, b, c and d of FIG. 2.

25. Process for preparing the crystalline molecular sieves of claim 23 having three-dimensional framework structures wherein the process comprises providing at an effective time at an effective temperature a reaction mixture composition expressed in terms of molar oxide ratios as follows:

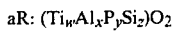

wherein "R" is an organic templating agent; "a" is an effective amount of "R" greater than zero to about 6; "b" has a value of from zero to about 500; and "w", "x", "y" and "z" represent the mole fractions, respectively, of titanium, aluminum, phosphorus and silicon in the $(Ti_wAl_xP_ySi_z)O_2$ constituent, and each has a value of at least 0.01, whereby molecular sieves according to claim 37 are prepared.

26. Process according to claim 25 wherein "w", "x", "y" and "z" are within the pentagonal area defined by points F, G, H, I and J of FIG. 3.

27. Process according to claim 25 wherein the source of phosphorus in the reaction mixture is orthophosphoric acid.

28. Process according to claim 25 wherein the source of phosphorus in the reaction mixture is orthophosphoric acid and the source of aluminum is at least one compound selected from the group of pseudo-boehmite and aluminum alkoxide.

29. Process according to claim 28 wherein the aluminum alkoxide is aluminum isopropoxide.

30. Process according to claim 28 wherein the source of silicon is silica.

31. Process according to claim 28 wherein the source of titanium is titanium acetate.

32. Process according to claim 25 or 26 wherein the organic templating agent is a quaternary ammonium or quaternary phosphonium compound having the formula:

$$R_4X^+$$

wherein X is nitrogen or phosphorus and each R is an alkyl or aryl group containing from 1 to 8 carbon atoms.

33. Process according to claim 25 wherein the organic templating agent is an amine.

34. Process according to claim 25 wherein the templating agent is selected from the group consisting of tetrapropylammoniumion; tetraethylammonium ion; tripropylamine; triethylamine; triethanolamine; piperidine; cyclohexylamine; 2-methyl pyridine; N,N-dimethylbenzylamine; N,N-dimethylethanolamine; choline; N,N-dimethylpiperazine; 1,4-diaziabicyclo-(2,2,2) octane; N-methyldiethanolamine; N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; tetramethylammonium ion; tetrabutylammonium ion; tetrapentylammonium ion; di-n-butylamine; neopentylamine; di-n-pentylamine; isopropylamine; t-butylamine; ethylenediamine; pyrrolidine; 2-imidazolidone; di-n-propylamine; and a polymeric quaternary ammonium salt $[(C_{14}H_{32}N_2)(OH)_2]_x$ wherein x has a value of at least 2.

35. Molecular sieve prepared by calcining the compositions of claim 23 or claim 24 at a temperature sufficiently high to remove at least some of any organic templating agent present in the intracrystalline pore system.

36. The crystalline molecular sieves of claim 23 or 24 wherein the values of "w", "x", "y" and "z" have the following mole fraction values: "w" is 0.01; and "z" is 0.04.

37. The process of claim 25 wherein "b" has a value of about 2 to about 500.

38. The process of claim 37 wherein "b" has a value of about 2 to about 300.

* * * * *